(12) United States Patent
Schaller et al.

(10) Patent No.: US 9,907,697 B2
(45) Date of Patent: *Mar. 6, 2018

(54) DELIVERY SYSTEM FOR OCULAR IMPLANT

(71) Applicant: Novartis AG, Basel (CH)

(72) Inventors: Michael Schaller, Menlo Park, CA (US); David Lari, Menlo Park, CA (US); Luke Clauson, Menlo Park, CA (US); Nathan White, Menlo Park, CA (US); Richard S. Lilly, Menlo Park, CA (US); Matthew Newell, Menlo Park, CA (US); Iqbal Ike K. Ahmed, Menlo Park, CA (US)

(73) Assignee: Novartis AG, Basel (CH)

( * ) Notice: Subject to any disclaimer, the term of this patent is extended or adjusted under 35 U.S.C. 154(b) by 102 days.

This patent is subject to a terminal disclaimer.

(21) Appl. No.: 15/005,745

(22) Filed: Jan. 25, 2016

(65) Prior Publication Data

US 2016/0135992 A1 May 19, 2016

Related U.S. Application Data

(63) Continuation of application No. 14/176,918, filed on Feb. 10, 2014, now Pat. No. 9,155,656, which is a
(Continued)

(51) Int. Cl.
*A61F 9/007* (2006.01)
*A61F 9/00* (2006.01)
(Continued)

(52) U.S. Cl.
CPC .......... *A61F 9/00781* (2013.01); *A61F 9/007* (2013.01); *A61F 9/0008* (2013.01);
(Continued)

(58) Field of Classification Search
CPC .. A61F 9/00781; A61F 9/0017; A61F 9/0008; A61F 9/007; A61F 2/95;
(Continued)

(56) References Cited

U.S. PATENT DOCUMENTS

| 2,990,670 A | 7/1961 | Kingsbury |
| 3,439,675 A | 4/1969 | Cohen |

(Continued)

FOREIGN PATENT DOCUMENTS

| CN | 1225027 A | 8/1999 |
| CN | 1285724 A | 2/2001 |

(Continued)

OTHER PUBLICATIONS

Schultz, David S. et al. "Structural Factors That Mediate Scleral Stiffness." Investigative Opthalmology & Visual Science. vol. 49, No. 10. Oct. 1, 2008 (Oct. 1, 2008). p. 4232,. XP055341369. US.

(Continued)

*Primary Examiner* — Adam Marcetich
(74) *Attorney, Agent, or Firm* — Mintz Levin Cohn Ferris Glovsky and Popeo, P.C.

(57) ABSTRACT

A delivery system is disclosed which can be used to deliver an ocular implant into a target location within the eye via an ab interno procedure. In some embodiments, the implant can provide fluid communication between the anterior chamber and the suprachoroidal or supraciliary space while in an implanted state. The delivery system can include a proximal handle component and a distal delivery component. In addition, the proximal handle component can include an actuator to control the release of the implant from the delivery component into the target location in the eye.

19 Claims, 6 Drawing Sheets

Related U.S. Application Data continuation of application No. 13/865,947, filed on Apr. 18, 2013, now Pat. No. 9,241,832.

(60) Provisional application No. 61/637,789, filed on Apr. 24, 2012.

(51) Int. Cl.

| | | |
|---|---|---|
| *A61M 25/09* | (2006.01) | |
| *A61F 2/95* | (2013.01) | |
| *A61F 9/008* | (2006.01) | |
| *A61M 5/32* | (2006.01) | |
| *A61M 5/20* | (2006.01) | |
| *A61F 2/16* | (2006.01) | |

(52) U.S. Cl.
CPC ........... *A61F 9/0017* (2013.01); *A61M 25/09* (2013.01); *A61M 25/0905* (2013.01); *A61F 2/167* (2013.01); *A61F 2/95* (2013.01); *A61F 2002/9505* (2013.01); *A61F 2002/9511* (2013.01); *A61F 2009/00891* (2013.01); *A61M 5/3257* (2013.01); *A61M 2005/206* (2013.01); *A61M 2025/09141* (2013.01); *A61M 2025/09175* (2013.01); *A61M 2025/09183* (2013.01); *A61M 2025/09191* (2013.01); *A61M 2210/0612* (2013.01)

(58) Field of Classification Search
CPC .... A61F 2009/00891; A61F 2002/9511; A61F 2002/9505; A61F 2/167; A61M 25/09; A61M 25/0905; A61M 2005/206; A61M 2025/09191; A61M 2025/09175; A61M 2025/09183; A61M 2025/09141; A61M 2210/0612; A61M 5/3257
See application file for complete search history.

(56) References Cited

U.S. PATENT DOCUMENTS

| | | |
|---|---|---|
| 3,767,759 A | 10/1973 | Wichterle |
| 3,788,327 A | 1/1974 | Donowitz et al. |
| 3,915,172 A | 10/1975 | Wichterle et al. |
| 4,037,604 A | 7/1977 | Newkirk |
| 4,402,681 A | 9/1983 | Haas et al. |
| 4,457,757 A | 7/1984 | Molteno |
| 4,521,210 A | 6/1985 | Wong |
| 4,554,918 A | 11/1985 | White |
| 4,604,087 A | 8/1986 | Joseph |
| 4,617,715 A | 10/1986 | Koistinen et al. |
| 4,634,418 A | 1/1987 | Binder |
| 4,722,724 A | 2/1988 | Schocket |
| 4,750,901 A | 6/1988 | Molteno |
| 4,787,885 A | 11/1988 | Binder |
| 4,826,478 A | 5/1989 | Schocket |
| 4,846,172 A | 7/1989 | Berlin |
| 4,863,457 A | 9/1989 | Lee |
| 4,886,488 A | 12/1989 | White |
| 4,900,300 A | 2/1990 | Lee |
| 4,930,512 A | 6/1990 | Henriksen et al. |
| 4,946,436 A | 8/1990 | Smith |
| 4,968,296 A | 11/1990 | Ritch et al. |
| 5,041,081 A | 8/1991 | Odrich |
| 5,071,408 A | 12/1991 | Ahmed |
| 5,073,163 A | 12/1991 | Lippman |
| 5,092,837 A | 3/1992 | Ritch et al. |
| 5,127,901 A | 7/1992 | Odrich |
| 5,171,213 A | 12/1992 | Price, Jr. |
| 5,178,604 A | 1/1993 | Baerveldt et al. |
| 5,180,362 A | 1/1993 | Worst |
| 5,284,476 A | 2/1994 | Koch |
| 5,300,020 A | 4/1994 | L'Esperance, Jr. |
| 5,338,291 A | 8/1994 | Speckman et al. |
| 5,342,370 A | 8/1994 | Simon et al. |
| 5,346,464 A | 9/1994 | Camras |
| 5,370,607 A | 12/1994 | Memmen |
| 5,372,577 A | 12/1994 | Ungerleider |
| 5,397,300 A | 3/1995 | Baerveldt et al. |
| 5,423,777 A | 6/1995 | Tajiri et al. |
| 5,433,701 A | 7/1995 | Rubinstein |
| 5,443,505 A | 8/1995 | Wong et al. |
| 5,454,746 A | 10/1995 | Guegan et al. |
| 5,476,445 A | 12/1995 | Baerveldt et al. |
| 5,497,782 A * | 3/1996 | Fugoso ............ A61M 25/0169 600/585 |
| 5,558,629 A | 9/1996 | Baerveldt et al. |
| 5,558,630 A | 9/1996 | Fisher |
| 5,569,197 A | 10/1996 | Helmus et al. |
| RE35,390 E | 12/1996 | Smith |
| 5,601,094 A | 2/1997 | Reiss |
| 5,626,558 A | 5/1997 | Suson |
| 5,626,559 A | 5/1997 | Solomon |
| 5,651,782 A | 7/1997 | Simon et al. |
| 5,676,944 A | 10/1997 | Alvarado et al. |
| 5,702,414 A | 12/1997 | Richter et al. |
| 5,704,907 A | 1/1998 | Nordquist et al. |
| 5,713,844 A | 2/1998 | Peyman |
| 5,741,292 A | 4/1998 | Mendius |
| 5,743,868 A | 4/1998 | Brown et al. |
| 5,749,879 A | 5/1998 | Middleman et al. |
| 5,752,928 A | 5/1998 | de Roulhac et al. |
| 5,792,075 A | 8/1998 | Schwager |
| 5,807,244 A | 9/1998 | Barot |
| 5,807,302 A | 9/1998 | Wandel |
| 5,868,697 A | 2/1999 | Richter et al. |
| 5,882,327 A | 3/1999 | Jacob |
| 5,893,837 A | 4/1999 | Eagles et al. |
| 5,921,918 A * | 7/1999 | Riza ................... A61B 17/0218 600/204 |
| 5,941,250 A | 8/1999 | Aramant et al. |
| 5,968,058 A | 10/1999 | Richter et al. |
| 6,007,510 A | 12/1999 | Nigam |
| 6,007,511 A | 12/1999 | Prywes |
| 6,036,678 A | 3/2000 | Giungo |
| 6,050,970 A | 4/2000 | Baerveldt |
| 6,050,999 A | 4/2000 | Paraschac et al. |
| 6,077,299 A | 6/2000 | Adelberg et al. |
| 6,102,045 A | 8/2000 | Nordquist et al. |
| 6,142,969 A | 11/2000 | Nigam |
| 6,152,918 A | 11/2000 | Padilla et al. |
| 6,174,307 B1 | 1/2001 | Daniel et al. |
| 6,186,974 B1 | 2/2001 | Allan et al. |
| 6,203,513 B1 | 3/2001 | Yaron et al. |
| 6,221,078 B1 | 4/2001 | Bylsma |
| 6,251,090 B1 | 6/2001 | Avery et al. |
| 6,261,256 B1 | 7/2001 | Ahmed |
| 6,264,668 B1 | 7/2001 | Prywes |
| 6,270,472 B1 | 8/2001 | Antaki et al. |
| 6,331,313 B1 | 12/2001 | Wong et al. |
| 6,375,642 B1 | 4/2002 | Grieshaber et al. |
| 6,383,219 B1 | 5/2002 | Telandro et al. |
| 6,450,984 B1 | 9/2002 | Lynch et al. |
| 6,464,724 B1 | 10/2002 | Lynch et al. |
| 6,468,283 B1 | 10/2002 | Richter et al. |
| 6,471,666 B1 | 10/2002 | Odrich |
| 6,471,777 B1 | 10/2002 | Kobayashi et al. |
| 6,494,857 B1 | 12/2002 | Neuhann |
| 6,508,779 B1 | 1/2003 | Suson |
| 6,510,600 B2 | 1/2003 | Yaron et al. |
| 6,524,275 B1 | 2/2003 | Lynch et al. |
| 6,533,768 B1 | 3/2003 | Hill |
| 6,537,568 B2 | 3/2003 | Olejnik et al. |
| 6,544,208 B2 | 4/2003 | Ethier et al. |
| 6,544,249 B1 | 4/2003 | Yu et al. |
| 6,558,342 B1 | 5/2003 | Yaron et al. |
| 6,561,974 B1 | 5/2003 | Grieshaber et al. |
| 6,579,256 B2 | 6/2003 | Hughes |
| 6,589,203 B1 | 7/2003 | Mitrev |
| 6,595,945 B2 | 7/2003 | Brown |
| 6,626,858 B2 | 9/2003 | Lynch et al. |
| 6,638,239 B1 | 10/2003 | Bergheim et al. |
| 6,648,283 B2 | 11/2003 | Chase et al. |
| 6,666,841 B2 | 12/2003 | Gharib et al. |

(56) References Cited

U.S. PATENT DOCUMENTS

| | | |
|---|---|---|
| 6,676,607 B2 | 1/2004 | de Juan, Jr. et al. |
| 6,699,210 B2 | 3/2004 | Williams et al. |
| 6,699,211 B2 | 3/2004 | Savage |
| 6,719,750 B2 | 4/2004 | Varner et al. |
| 6,726,664 B2 | 4/2004 | Yaron et al. |
| 6,726,676 B2 | 4/2004 | Stegmann et al. |
| 6,730,056 B1 | 5/2004 | Ghaem et al. |
| 6,736,791 B1 | 5/2004 | Tu et al. |
| 6,741,666 B1 | 5/2004 | Henry et al. |
| 6,752,753 B1 | 6/2004 | Hoskins et al. |
| 6,780,164 B2 | 8/2004 | Bergheim et al. |
| 6,783,544 B2 | 8/2004 | Lynch et al. |
| 6,786,888 B1 | 9/2004 | Zadno-Azizi et al. |
| 6,827,699 B2 | 12/2004 | Lynch et al. |
| 6,827,700 B2 | 12/2004 | Lynch et al. |
| 6,881,197 B1 | 4/2005 | Nigam |
| 6,881,198 B2 | 4/2005 | Brown |
| 6,939,298 B2 | 9/2005 | Brown et al. |
| 6,955,656 B2 | 10/2005 | Bergheim et al. |
| 6,962,573 B1 | 11/2005 | Wilcox |
| 6,966,888 B2 | 11/2005 | Cullen et al. |
| 6,969,384 B2 | 11/2005 | de Juan, Jr. et al. |
| 6,981,958 B1 | 1/2006 | Gharib et al. |
| 6,989,007 B2 | 1/2006 | Shadduck |
| 7,041,077 B2 | 5/2006 | Shields |
| 7,090,681 B2 | 8/2006 | Weber et al. |
| 7,094,225 B2 | 8/2006 | Tu et al. |
| 7,135,009 B2 | 11/2006 | Tu et al. |
| 7,160,264 B2 | 1/2007 | Lisk, Jr. et al. |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,195,774 B2 | 3/2007 | Carvalho et al. |
| 7,207,965 B2 | 4/2007 | Simon |
| 7,220,238 B2 | 5/2007 | Lynch et al. |
| 7,273,475 B2 | 9/2007 | Tu et al. |
| 7,291,125 B2 | 11/2007 | Coroneo |
| 7,297,130 B2 | 11/2007 | Bergheim et al. |
| 7,331,984 B2 | 2/2008 | Tu et al. |
| 7,431,710 B2 | 10/2008 | Tu et al. |
| 7,488,303 B1 | 2/2009 | Haffner et al. |
| 7,563,241 B2 | 7/2009 | Tu et al. |
| 7,708,711 B2 | 5/2010 | Tu et al. |
| 7,850,637 B2 | 12/2010 | Lynch et al. |
| 7,857,782 B2 | 12/2010 | Tu et al. |
| 7,867,186 B2 | 1/2011 | Haffner et al. |
| 7,867,205 B2 | 1/2011 | Bergheim et al. |
| 7,972,616 B2 | 7/2011 | Dubrow et al. |
| 8,075,511 B2 | 12/2011 | Tu et al. |
| 8,128,588 B2 | 3/2012 | Coroneo |
| 8,142,413 B2 | 3/2012 | Root et al. |
| 8,172,899 B2 | 5/2012 | Silvestrini et al. |
| 8,292,850 B2 | 10/2012 | Root et al. |
| 8,337,393 B2 | 12/2012 | Silverstrini et al. |
| 8,702,727 B1 | 4/2014 | Harrington et al. |
| 8,721,656 B2 | 5/2014 | De Juan, Jr. et al. |
| 9,155,656 B2 * | 10/2015 | Schaller ............... A61F 9/00781 |
| 2002/0013546 A1 | 1/2002 | Grieshaber et al. |
| 2002/0013572 A1 | 1/2002 | Berlin |
| 2002/0072673 A1 | 6/2002 | Yamamoto et al. |
| 2002/0087111 A1 | 7/2002 | Ethier et al. |
| 2002/0111608 A1 | 8/2002 | Baerveldt et al. |
| 2002/0128613 A1 | 9/2002 | Nakayama |
| 2002/0133168 A1 | 9/2002 | Smedley et al. |
| 2002/0143284 A1 | 10/2002 | Tu et al. |
| 2002/0177856 A1 | 11/2002 | Richter et al. |
| 2002/0188308 A1 | 12/2002 | Tu et al. |
| 2002/0193725 A1 | 12/2002 | Odrich |
| 2002/0193804 A1 | 12/2002 | Tickle |
| 2003/0028127 A1 | 2/2003 | Balzum et al. |
| 2003/0028228 A1 | 2/2003 | Sand |
| 2003/0055372 A1 | 3/2003 | Lynch et al. |
| 2003/0060752 A1 | 3/2003 | Bergheim et al. |
| 2003/0097151 A1 | 5/2003 | Smedley et al. |
| 2003/0097171 A1 | 5/2003 | Elliott |
| 2003/0109883 A1 | 6/2003 | Matsuzaki et al. |
| 2003/0135149 A1 | 7/2003 | Cullen et al. |
| 2003/0181848 A1 | 9/2003 | Bergheim et al. |
| 2003/0187384 A1 | 10/2003 | Bergheim et al. |
| 2003/0208163 A1 | 11/2003 | Yaron et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0015140 A1 | 1/2004 | Shields |
| 2004/0024345 A1 | 2/2004 | Gharib et al. |
| 2004/0088048 A1 | 5/2004 | Richter et al. |
| 2004/0092856 A1 | 5/2004 | Dahan |
| 2004/0097984 A1 | 5/2004 | Zapata |
| 2004/0102729 A1 | 5/2004 | Haffner et al. |
| 2004/0106977 A1 | 6/2004 | Sullivan et al. |
| 2004/0111050 A1 | 6/2004 | Smedley et al. |
| 2004/0127843 A1 | 7/2004 | Tu et al. |
| 2004/0147870 A1 | 7/2004 | Burns et al. |
| 2004/0148022 A1 | 7/2004 | Eggleston |
| 2004/0193095 A1 | 9/2004 | Shadduck |
| 2004/0193262 A1 | 9/2004 | Shadduck |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225250 A1 | 11/2004 | Yablonski |
| 2004/0236343 A1 | 11/2004 | Taylor et al. |
| 2004/0249333 A1 | 12/2004 | Bergheim et al. |
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0254521 A1 | 12/2004 | Simon |
| 2004/0260228 A1 | 12/2004 | Lynch et al. |
| 2005/0008673 A1 | 1/2005 | Snyder et al. |
| 2005/0049578 A1 | 3/2005 | Tu et al. |
| 2005/0085892 A1 | 4/2005 | Goto et al. |
| 2005/0090806 A1 | 4/2005 | Lynch et al. |
| 2005/0090807 A1 | 4/2005 | Lynch et al. |
| 2005/0101967 A1 | 5/2005 | Weber et al. |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0119737 A1 | 6/2005 | Bene et al. |
| 2005/0125003 A1 | 6/2005 | Pinchuk et al. |
| 2005/0143817 A1 | 6/2005 | Hunter et al. |
| 2005/0149080 A1 | 7/2005 | Hunter et al. |
| 2005/0171507 A1 | 8/2005 | Christian et al. |
| 2005/0175663 A1 | 8/2005 | Hunter et al. |
| 2005/0181011 A1 | 8/2005 | Hunter et al. |
| 2005/0181977 A1 | 8/2005 | Hunter et al. |
| 2005/0182350 A1 | 8/2005 | Nigam |
| 2005/0191331 A1 | 9/2005 | Hunter et al. |
| 2005/0192527 A1 | 9/2005 | Gharib et al. |
| 2005/0197613 A1 | 9/2005 | Sniegowski et al. |
| 2005/0209549 A1 | 9/2005 | Bergheim et al. |
| 2005/0209550 A1 | 9/2005 | Bergheim et al. |
| 2005/0209555 A1 | 9/2005 | Middleton et al. |
| 2005/0232972 A1 | 10/2005 | Odrich |
| 2005/0244462 A1 | 11/2005 | Farooq |
| 2005/0245911 A1 | 11/2005 | Wright et al. |
| 2005/0250788 A1 | 11/2005 | Tu et al. |
| 2005/0266047 A1 | 12/2005 | Tu et al. |
| 2005/0267397 A1 | 12/2005 | Bhalla |
| 2005/0267398 A1 | 12/2005 | Protopsaltis et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0283108 A1 | 12/2005 | Savage |
| 2005/0287188 A1 | 12/2005 | Anderson et al. |
| 2005/0288617 A1 | 12/2005 | Yaron et al. |
| 2005/0288619 A1 | 12/2005 | Gharib et al. |
| 2006/0004348 A1 | 1/2006 | Scheller et al. |
| 2006/0020248 A1 | 1/2006 | Prescott |
| 2006/0032507 A1 | 2/2006 | Tu |
| 2006/0036207 A1 | 2/2006 | Koonmen et al. |
| 2006/0069340 A1 | 3/2006 | Simon |
| 2006/0074375 A1 | 4/2006 | Bergheim et al. |
| 2006/0084907 A1 | 4/2006 | Bergheim et al. |
| 2006/0116626 A1 | 6/2006 | Smedley et al. |
| 2006/0149194 A1 | 7/2006 | Conston et al. |

(56) References Cited

U.S. PATENT DOCUMENTS

| | | |
|---|---|---|
| 2006/0155238 A1 | 7/2006 | Shields |
| 2006/0173397 A1 | 8/2006 | Tu et al. |
| 2006/0195055 A1 | 8/2006 | Bergheim et al. |
| 2006/0195056 A1 | 8/2006 | Bergheim et al. |
| 2006/0200113 A1 | 9/2006 | Haffner et al. |
| 2006/0235367 A1 | 10/2006 | Takashima et al. |
| 2006/0241580 A1 | 10/2006 | Mittelstein et al. |
| 2006/0241749 A1 | 10/2006 | Tu et al. |
| 2006/0276739 A1 | 12/2006 | Brown |
| 2007/0010827 A1 | 1/2007 | Tu et al. |
| 2007/0088242 A1 | 4/2007 | Coroneo |
| 2007/0088424 A1 | 4/2007 | Greenberg et al. |
| 2007/0088432 A1 | 4/2007 | Solovay et al. |
| 2007/0106235 A1 | 5/2007 | Coroneo |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0129717 A1 | 6/2007 | Brown et al. |
| 2007/0141106 A1 | 6/2007 | Bonutti et al. |
| 2007/0149915 A1 | 6/2007 | Yablonski |
| 2007/0191863 A1 | 8/2007 | De Juan et al. |
| 2007/0207186 A1 | 9/2007 | Scanlon et al. |
| 2007/0233037 A1 | 10/2007 | Gifford et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2008/0015488 A1 | 1/2008 | Tu et al. |
| 2008/0045878 A1 | 2/2008 | Bergheim et al. |
| 2008/0058704 A1 | 3/2008 | Hee et al. |
| 2008/0108933 A1 | 5/2008 | Yu et al. |
| 2008/0147021 A1 | 6/2008 | Jani |
| 2008/0151188 A1 | 6/2008 | Kawai et al. |
| 2008/0195027 A1 | 8/2008 | Coroneo |
| 2008/0200860 A1 | 8/2008 | Tu et al. |
| 2008/0228127 A1 | 9/2008 | Burns et al. |
| 2008/0234624 A2 | 9/2008 | Bergheim et al. |
| 2009/0036819 A1 | 2/2009 | Tu et al. |
| 2009/0036840 A1 | 2/2009 | Viray et al. |
| 2009/0043321 A1 | 2/2009 | Conston et al. |
| 2009/0118702 A1 | 5/2009 | Lazar |
| 2009/0171358 A1 | 7/2009 | Chang et al. |
| 2009/0182421 A1 | 7/2009 | Silvestrini et al. |
| 2009/0318947 A1* | 12/2009 | Garcia ............. A61B 17/12022 606/191 |
| 2010/0010416 A1 | 1/2010 | Juan, Jr. et al. |
| 2010/0134759 A1 | 6/2010 | Silvestrini et al. |
| 2010/0137981 A1 | 6/2010 | Silvestrini et al. |
| 2010/0152641 A1 | 6/2010 | Yablonski |
| 2010/0211079 A1 | 8/2010 | Aramant |
| 2010/0234790 A1 | 9/2010 | Tu et al. |
| 2010/0274259 A1 | 10/2010 | Yaron et al. |
| 2010/0280317 A1 | 11/2010 | Silvestrini et al. |
| 2011/0028883 A1 | 2/2011 | Juan, Jr. et al. |
| 2011/0028884 A1 | 2/2011 | Theodore Coroneo |
| 2011/0087148 A1 | 4/2011 | Silvestrini et al. |
| 2011/0087149 A1 | 4/2011 | Theodore Coroneo |
| 2011/0087150 A1 | 4/2011 | Theodore Coroneo |
| 2011/0087151 A1 | 4/2011 | Theodore Coroneo |
| 2011/0098629 A1 | 4/2011 | Juan, Jr. et al. |
| 2011/0098809 A1 | 4/2011 | Wardle et al. |
| 2011/0112546 A1 | 5/2011 | Juan, Jr. et al. |
| 2011/0196396 A1* | 8/2011 | Richter ............ A61B 17/22012 606/159 |
| 2011/0230856 A1 | 9/2011 | Kyle et al. |
| 2011/0238075 A1 | 9/2011 | Clauson et al. |
| 2011/0276054 A1 | 11/2011 | Helmy |
| 2011/0288525 A1 | 11/2011 | Hallen et al. |
| 2011/0306915 A1 | 12/2011 | De Juan, Jr. et al. |
| 2011/0313271 A1* | 12/2011 | Schulman ............ A61B 5/04001 600/386 |
| 2012/0035524 A1 | 2/2012 | Silvestrini |
| 2012/0035525 A1 | 2/2012 | Silvestrini |
| 2012/0046575 A1* | 2/2012 | Brown ................. A61M 25/09 600/585 |
| 2012/0065670 A1 | 3/2012 | Tiedtke et al. |
| 2012/0089071 A1 | 4/2012 | Oliver et al. |
| 2012/0116504 A1 | 5/2012 | Lyons et al. |
| 2012/0123316 A1 | 5/2012 | Horvath et al. |
| 2012/0123433 A1 | 5/2012 | Horvath et al. |
| 2012/0123434 A1 | 5/2012 | Grabner et al. |
| 2012/0220917 A1 | 8/2012 | Silvestrini et al. |
| 2012/0271272 A1 | 10/2012 | Hammack et al. |
| 2013/0245532 A1 | 9/2013 | Tu |
| 2013/0281817 A1 | 10/2013 | Schaller et al. |
| 2013/0281908 A1 | 10/2013 | Schaller et al. |
| 2013/0281910 A1 | 10/2013 | Tu |
| 2014/0012279 A1 | 1/2014 | de Juan, Jr. et al. |
| 2014/0066831 A1 | 3/2014 | Silvestrini et al. |
| 2014/0081195 A1 | 3/2014 | Clauson et al. |
| 2014/0107556 A1 | 4/2014 | Silvestrini et al. |
| 2014/0135916 A1 | 5/2014 | Clauson et al. |
| 2014/0155805 A1 | 6/2014 | Schaller et al. |
| 2014/0213958 A1 | 7/2014 | Clauson et al. |
| 2014/0323995 A1 | 10/2014 | Clauson et al. |
| 2014/0364789 A1 | 12/2014 | Schaller |
| 2014/0378886 A1 | 12/2014 | de Juan, Jr. et al. |
| 2015/0022780 A1 | 1/2015 | John et al. |
| 2015/0223982 A1 | 8/2015 | Yablonski |
| 2015/0238360 A1 | 8/2015 | de Juan, Jr. et al. |
| 2015/0320596 A1 | 11/2015 | Gifford, III et al. |
| 2015/0335487 A1 | 11/2015 | de Juan, Jr. |

FOREIGN PATENT DOCUMENTS

| | | |
|---|---|---|
| CN | 1124164 C | 10/2003 |
| CN | 1681457 A | 10/2005 |
| EP | 0 228 185 A1 | 11/1986 |
| EP | 1184010 A2 | 3/2002 |
| EP | 1310222 A2 | 5/2003 |
| EP | 1473004 A2 | 11/2004 |
| EP | 1477146 A2 | 11/2004 |
| EP | 1418868 B1 | 3/2008 |
| EP | 1977724 A1 | 10/2008 |
| EP | 2027837 A2 | 2/2009 |
| GB | 2101891 A | 1/1983 |
| JP | 2007-535386 A | 12/2007 |
| JP | 2010-533565 A | 10/2010 |
| RU | 2018289 C1 | 8/1994 |
| RU | 2056818 C1 | 3/1996 |
| RU | 2074686 C1 | 3/1997 |
| RU | 2074687 C1 | 3/1997 |
| RU | 2157678 C1 | 10/2000 |
| RU | 2010121933 A | 12/2011 |
| WO | WO-89/00869 A1 | 2/1989 |
| WO | WO-91/12046 A1 | 8/1991 |
| WO | WO-92/19294 A1 | 11/1992 |
| WO | WO-94/02081 A1 | 2/1994 |
| WO | WO-94/09721 A1 | 5/1994 |
| WO | WO-94/09837 A1 | 5/1994 |
| WO | WO-94/10900 A1 | 5/1994 |
| WO | WO-94/13234 A1 | 6/1994 |
| WO | WO-95/08310 A1 | 3/1995 |
| WO | WO-96/20742 A1 | 7/1996 |
| WO | WO-96/36377 A1 | 11/1996 |
| WO | WO 97/44085 A2 | 11/1997 |
| WO | WO-98/23237 A1 | 6/1998 |
| WO | WO-98/30181 A1 | 7/1998 |
| WO | WO-99/26567 A1 | 6/1999 |
| WO | WO-00/06223 A1 | 2/2000 |
| WO | WO-00/64389 A1 | 11/2000 |
| WO | WO-00/64390 A1 | 11/2000 |
| WO | WO-00/64391 A1 | 11/2000 |
| WO | WO-00/64393 A1 | 11/2000 |
| WO | WO-00/64511 A1 | 11/2000 |
| WO | WO-01/68016 A2 | 9/2001 |
| WO | WO-01/78631 A2 | 10/2001 |
| WO | WO-01/78656 A2 | 10/2001 |
| WO | WO-01/97727 A1 | 12/2001 |
| WO | WO-02/36052 A1 | 5/2002 |
| WO | WO-02/070045 A1 | 9/2002 |
| WO | WO-02/074052 A2 | 9/2002 |

(56) References Cited

FOREIGN PATENT DOCUMENTS

| | | |
|---|---|---|
| WO | WO-02/080811 A2 | 10/2002 |
| WO | WO-02/080829 A2 | 10/2002 |
| WO | WO-02/087418 A2 | 11/2002 |
| WO | WO-02/087479 A2 | 11/2002 |
| WO | WO-02/089699 A2 | 11/2002 |
| WO | WO-02/102274 A2 | 12/2002 |
| WO | WO-03/015659 A2 | 2/2003 |
| WO | WO-03/015667 A1 | 2/2003 |
| WO | WO-03/041622 A2 | 5/2003 |
| WO | WO-03/073968 A2 | 9/2003 |
| WO | WO-03/096871 A2 | 11/2003 |
| WO | WO-03/099175 A1 | 12/2003 |
| WO | WO-2004/014218 A2 | 2/2004 |
| WO | WO-2004/026106 A2 | 4/2004 |
| WO | WO-2004/026347 A2 | 4/2004 |
| WO | WO-2004/043231 A2 | 5/2004 |
| WO | WO-2004/056294 A1 | 7/2004 |
| WO | WO-2004/060219 A1 | 7/2004 |
| WO | WO-2004/062469 A2 | 7/2004 |
| WO | WO-2004/066871 A2 | 8/2004 |
| WO | WO-2004/073552 A2 | 9/2004 |
| WO | WO-2004/110391 A2 | 12/2004 |
| WO | WO-2005/016418 A1 | 2/2005 |
| WO | WO-2005/046782 A1 | 5/2005 |
| WO | WO-2005/055873 A2 | 6/2005 |
| WO | WO-2005/105197 A2 | 11/2005 |
| WO | WO-2005/107664 A2 | 11/2005 |
| WO | WO-2005/107845 A1 | 11/2005 |
| WO | WO-2006/012421 A2 | 2/2006 |
| WO | WO-2006/036715 A2 | 4/2006 |
| WO | WO-2007/087061 A2 | 8/2007 |
| WO | WO-2007/115259 A2 | 10/2007 |
| WO | WO-2007/130393 A2 | 11/2007 |
| WO | WO-2008/061043 | 5/2008 |
| WO | WO-2009/012406 A1 | 1/2009 |
| WO | WO-2009/035562 A2 | 3/2009 |
| WO | WO-2009/058929 A1 | 5/2009 |
| WO | WO-2009/158524 A2 | 12/2009 |
| WO | WO-2010/065970 A1 | 6/2010 |
| WO | WO-2010/115101 A1 | 10/2010 |
| WO | WO-2012/019136 A2 | 2/2012 |

OTHER PUBLICATIONS

PCT/IB2016/001422, Sep. 16, 2016, WO 2017/051247.
U.S. Appl. No. 14/199,737, filed Mar. 6, 2014, 2014-0188030.
U.S. Appl. No. 14/809,827, filed Jul. 27, 2015, 2016-0022486.
Barsky et al. "Evaluation of absorbable gelatin film (Gelfilm) in cyclodialysis clefts" Arch. Ophth. 60(6): 1044-1052, 1958.
Bick MW "Use of tantalum for ocular drainage" Arch Ophthal. 42(4): 373-88 (1949).
Bietti "The present state of the use of plastics in eye surgery" Acta Ophthalmol (Copenh) 33(4):337-70 (1955).
Brown et al., "Internal Sclerectomy for Glaucoma Filtering Surgery with an Automated Trephine," Archives of Ophthalmology, 105:133-136 (1987).
Burchfield JC, Kass MA, Wax MB. Primary valve malfunction of the Krupin eye valve with disk. J Glaucoma. Jun. 1997;6(3):152-6.
Chiou et al. "Ultrasound biomicroscopy of eyes undergoing deep sclerectomy with collagen implant" Br J Ophthalmol 80 (1996), pp. 541-544.
Chylack LT, Bellows AR. Molecular sieving in suprachoroidal fluid formation in man. Invest Ophthalmol Vis Sci 17: 420, 1978.
Classen et al. "A histopathologic and immunohistorchemical analysis of the filtration bleb after unsuccessful glaucoma seton implantation" Am. J. Ophthalmol. 122:205-12 (1996).
Cohen et al. "First day post-operative review following uncomplicated phacoemulsification" Eye 12(4):634-6 (1998).
Collaborative Normal-Tension Study Group. Comparison of glaucomatous progression between untreated patients with normal-tension glaucoma and patients with therapeutically reduced intraocular pressures. Am J Ophthalmol 1998;126:487-97.

Congdon N, O'Colmain B, Klaver CC, et al. Causes and prevalence of visual impairment among adults in the United States. Arch Ophthalmol 2004;122:477-85.
Coote. "Glaucoma Hollow Fiber Filters—A New Glaucoma Seton. Preliminary Results." *J. Glaucoma*. vol. 8 No. 1 Supplement (1999):p. S4.
Cullen, et al. "Anterior Chamber of Frontal Sinus Shunt for the Diversion of Aqueous Humor: A Pilot Study in Four Normal Dogs". *Veterinary Ophthalmology*. vol. 1. No. 1. (1998):31-39.
Demailly et al. "Non-penetrating deep sclerectomy (NPDS) with or without collagen device (CD) in primary open-angle glaucoma: middle-term retrospective study" International Ophthalmology 20: 131-140, 1997.
Derwent English abstract for EP 1184010, published Mar. 6, 2002 entitled: "Drainage unit for an eye, consists of a hollow line, a distribution member, and a pressure relief valve which only allows water to leave the eye chamber above a certain pressure," Accession Nbr. 12409716 [351].
Dinakaran et al. "Is the first post-operative day review necessary following uncomplicated phacoemulsification surgery?" Eye, 14(3A):364-6 (2000).
Draeger "Chirurgische Maβnahmen bei kongenitalem Glaukom" (Surgical Interventions in Congenital Glaucoma) Klin Monatsbl Augenheilkd 1993; 202(5): 425-427 [Article in German with English summary included].
Einmahl et al. "Evaluation of a novel biomaterial in the suprachoroidal space of the rabbit eye" Invest Ophthalmol Vis Sci. 43:1533-1539 (2002).
Ellis, RA "A Reduction of Intraocular Pressure Using Plastics in Surgery" Am J Ophth. 50; 1960, 733-742.
Emi et al. "Hydrostatic pressure of the suprachoroidal space" Invest. Ophthal. Visual Sci. 30(2):233-238 (1989).
Fanous MM, Cohn RA. Propionibacterium endophthalmitis following Molteno tube repositioning. J Glaucoma. Aug. 1997;6(4):201-2.
Friedman DS, Wolfs RC, O'Colmain BJ, et al. Prevalence of open-angle glaucoma among adults in the United States. Arch Ophthalmol 2004;122:532-8.
Fuchs E. "Detachment of the choroid inadvertently during cataract surgery" [German] von Graefes Arch Ophthalmol, 51:199-224 (1900) [Article in German with English summary].
Gills et al. "Action of cyclodialysis utilizing an implant studied by manometry in a human eye" Exp Eye Res 1967; 6:75-78.
Gills JP "Cyclodialysis implants" South Med J. 1967 60(7):692-5.
Gills, "Cyclodialysis Implants in Human Eyes" Am J Ophth 61:1966,841-846.
Goldberg "Management of Uncontrolled Glaucoma With the Molteno System" Australian and New Zealand Journal of Ophthalmology 1987; 15: 97-107.
Gordon MO, Kass. MA, for the Ocular Hypertension Treatment Study Group. The Ocular Hypertension Treatment Study. Design and baseline description of the participants. Arch Ophthalmol 1999:573-83.
Grant, W.M. , MD, Further Studies on Facility of Flow Through the Trabecular Meshwork, A.M.A. Archives of Ophthalmololgy, Oct. 1958, vol. 60, pp. 523-533.
Gross et al. "Surgical therapy of chronic glaucoma in aphakia and pseudophakia" Ophthalmology, 95:1195-201 (1988).
Harper SL, Foster CS. Intraocular lens explantation in uveitis. Int Ophthalmol Clin. 2000 Winter; 40(1):107-16.
Harrington "Cataract and Glaucoma. Management of the coexistent conditions and a description of a new operation combining lens extraction with reverse cyclodialysis." Am J Ophthalmol. May 1966; 61(5 Pt 2):1134-40.
Heijl A, Leske MC, Bengtsson B, et al for the Early Manifest Glaucoma Trial Group. Reduction of intraocular pressure and glaucoma progression. Results from the Early Manifest Glaucoma Trial. Arch Ophthalmol 2002;120:1268-79.
Heine I. "Cyclodialysis, a new glaucoma operation" [German] Dtsch Med Wochenschr, 31:824-826 (1905).
Hildebrand et al. "Efficacy of anterior chamber decompression in controlling early intraocular pressure spikes after uneventful phacoemulsification" J. Catact Refract Surg., 29:1087-92 (2003).

(56) References Cited

OTHER PUBLICATIONS

Hoskins, et al., "Aqueous Humor Outflow", Becker-Shaffer's Diagnosis and Therapy of the Glaucomas, 6th Edition, Chapter 4, pp. 41-66, 1989.

Howorth D J "Feasibility study for a micromachined glaucoma drainage device" Cranfield University School of industrial and manufacturing science MSc Thesis Academic Year 2001-2002 Sep. 13, 2002.

Hylton et al. "Update on prostaglandin analogs" Curr Opin Ophthalmol, 14:65-9 (2003).

In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Colin Clement in support of Opponent's opposition. (Sep. 9, 2014).

In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Ilesh Patel in support of Opponent's opposition. (Sep. 9, 2014).

In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Mr. Craig Andrews in support of Opponent's opposition. (Sep. 9, 2014).

In the Commonwealth of Australia—In the Matter of Australian Patent Application No. 2006336598 in the name of Transcend Medical, Inc. ("Applicant") and Opposition thereto by Glaukos Corporation ("Opponent")—Opponent's amended Statement of Grounds and Particulars of Opposition. (Sep. 10, 2014).

In the Commonwealth of Australia—In the Matter of Australian Patent Application No. 2006336598 in the name of Transcend Medical, Inc. ("Applicant") and Opposition thereto by Glaukos Corporation ("Opponent"), Commonwealth of Australia—Opponent's Statement of Grounds and Particulars of Opposition. (Apr. 10, 2014).

In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Robert L. Stamper in support of Applicant's Evidence in Answer. (Dec. 4, 2014).

In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Jonathan G. Crowston in support of Applicant's Evidence in Answer. (Dec. 6, 2014).

In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Anne Jen-Wan Lee in support of Applicant's Evidence in Answer. (Dec. 7, 2014).

In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Colin Clement in support of Opponent's Evidence in Reply. (Feb. 8, 2015).

In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Dr. Ilesh Patel in support of Opponent's Evidence in Reply. (Feb. 10, 2015).

In the Commonwealth of Australia—In the Matter of Australian Patent Application No. 2006336598 in the name of Transcend Medical, Inc. ("Applicant") and Opposition thereto by Glaukos Corporation ("Opponent")—Declaration of Mr. Craig Andrews in support of Opponent's Evidence in Reply. (Feb. 11, 2015).

Javitt JC, Chiang YP. Preparing for managed competition. Utilization of ambulatory eye care visits to ophthalmologists. Arch Ophthalmol 1993;111:1034-5.

Jay JL, Allan D. The benefit of early trabeculectomy versus conventional management in primary open-angle glaucoma relative to severity of disease. Eye 1989; 3:528-35.

Jordan J. "A Novel Approach to Suprachoroidal Drainage for the Surgical Treatment of Intractable Glaucoma" J. Glaucoma 15:200-205 (2006).

Jordan JF, Dietlein TS, Dinslage S, Luke C, Konen W, Krieglstein GK. Cyclodialysis ab inferno as a surgical approach to intractable glaucoma. Graefes Arch Clin Exp Ophthalmol. Aug. 2007;245(8):1071-6.

Karlen et al. "Deep sclerectomy with collagen implant: medium term results" Br. J. Ophthalmol, Jan. 1999, 83(1):6-11.

Kass MA, Heuer DK, Higginbotham EJ, et al for the Ocular Hypertension Treatment Study Group. The Ocular HypertensionTreatment Study. A randomized trial determines that topical ocular hypotensive medication delays or prevents the onset of primary open-angle glaucoma. Arch Ophthalmol 2002;120:701-13.

Klemm et al. "Die Ultraschallbiomikroskopie als Kriterium der Funktionsprüfung des suprachorioidalen Spaltes nach kammerwinkelchirurgischen Eingriffen" (Ultrasound Biomicroscopic Imaging for Assessment of the Suprachoroidal Cleft after Angle Surgery)"Klinische Monatsblätter für Augenheilkunde 1997; 210: 74-77 [Article in German with English summary included]".

Klemm et al. "Experimental use of space-retaining substances with extended duration: functional and morphological results" Graefes Arch Clin Exp Ophthalmol Sep. 1995; 233(9):592-7.

Kozlov et al. "Nonpenetrating deep sclerectomy with collagen" Eye microsurgery 3:44-46 (1990) [Russian with English translation].

Krejci "Cyclodialysis with hydroxymethyl methacrylate capillary strip (HCS). Animal experiments with a new approach in glaucoma drainage surgery" Ophthalmologica 1972; 164(2):113-21.

Krejci L. "Microdrainage of anterior chamber of eye glaucoma operation using hydron capillary drain. " Acta Univ Carol Med Monogr. 1974;(61):1-90.

Kupfer "Studies on intraocular pressure. I. A technique for polyethylene tube implantation into the anterior chamber of the rabbit." Arch Ophthalmol. Apr. 1961;65:565-70.

La Rocca "Gonioplasty in Glaucoma*A Preliminary Report" Br J Ophth 46:1962, 404-415.

Law et al., "Retinal Complications After Aqueous Shunt Surgical Procedures for Glaucoma" Arch Ophthal.; Dec. 1996; vol. 114:1473-1480.

Lee et al. "Aqueous-venous shunt and intraocular pressure. Preliminary report of animal studies." *Investigative Ophthalmology*. vol. 5 No. 1: 59-64. Feb. 1966.

Lee et al. "Magnetic resonance imaging of the aqueous flow in eyes implanted with the trabeculo-suprachoroidal glaucoma seton" Invest. Ophthalmol. Vis. Sci. 33:948 (1992).

Lee KY. Trabeculo-suprachoroidal shunt for treating recalcitrant and secondary glaucoma. Presented at the American Academy of Ophthalmology Annual Meeting, Anaheim, CA, 1991.

Leske MC, Heijl A, Hussein M, et al for the Early Manifest Glaucoma Trial Group. Factors for glaucoma progression and the effect of treatment. The Early Manifest Glaucoma Trial. Arch Ophthalmol Jan. 2003;121:48-56.

Lichter PR, Musch DC, Gillespie BW, et al and the CIGTS Study Group. Interim clinical outcomes in the Collaborative Initial Glaucoma Treatment Study comparing initial treatment randomized to medications or surgery. Ophthalmology 2001;108:1943-53.

Losche W. "Proposals for improvement of cyclodialysis Klin Monatsblatter Augenheilkd Augenarztl Fortbild" 121(6):715-6 (1952) [German].

Marx et al., "Use of the Ganciclovir Implant in the Treatment of Recurrent Cytomegalovirus Retinitis" Arch Ophthal.; Jul. 1996; vol. 114:815-820.

McPherson "Combined Trabeculotomy and Cataract Extraction as a Single Operation" Tr. Am. Ophth. Soc., vol. LXXIV, 1976; 251-260.

Migdal C, Gregory W, Hitchings R. Long term functional outcome after early surgery compared with laser and medicine in open-angle glaucoma. Ophthalmology 1994;101:1651-7.

(56) References Cited

OTHER PUBLICATIONS

Miglior S, Pfeiffer N, Zeyen T et al for the European Glaucoma Prevention Study Group. Results of the European Glaucoma Prevention Study. Ophthalmology 2005;112:366-75.

Miglior S, Zeyen T, Pfeiffer N, et al for the European Glaucoma Prevention Study Group. The European Glaucoma Prevention Study design and baseline description of the participants. Ophthalmology 2002;109:1612-21.

Miki, MD et al., "Intraocular Cannula for Continuous, Chronic Drug Delivery-Histopathic Observations and Function" Arch Ophthal.; May 1985; vol. 103:712-717.

Molteno et al. "Long tube implants in the management of glaucoma" South African Medical Journal, Jun. 26, 1976;50(27):1062-6.

Molteno et al. "The Vicryl tie technique for inserting a draining implant in the treatment of secondary glaucoma." Australian and New Zealand Journal of Ophthalmology 1986; 14: 343-354.

Moses RA "Detachment of ciliary body-anatomical and physical considerations" Investigative Ophthalmology & Visual Science, Assoc. for Research in Vision and Ophthalmology, US, vol. 4, No. 5, Oct. 1, 1965.

Nesterov AP et al. "Surgical stimulation of the uveoscleral outflow. Experimental studies on enucleated human eyes" Acta Opthalmol (Copenh) Jun.; 57(3):409-17 (1979).

Nguyen et al., "Complications of Baerveldt Glaucoma Drainage Implants" Arch Ophthal.; May 1998; vol. 116:571-575.

Noecker RJ. Clinical Evaluation of a Novel Gold Micro-Shunt for Reduction of 10 P in Refractory Glaucomas. American Glaucoma Society Annual Meeting, San Francisco, CA, 2007.http://www.glaucomaweb.org/associations/5224/files/AGS%20AMO7%20Prgrm%20FINAL.pdf. Accessed Nov. 1, 2008).

O'Brien et al. "Cyclodialysis" Arch Ophthal. 1949;42(5):606-619.

Odrich. "The New Technique During Complex Tube-Shunt Implantation". *J. Glaucoma.* vol. 9 No. 3 (2000):278-279.

Olsen, Timothy W., et al., Cannulation of the Suprachoroidal Space: A Novel Drug Delivery Methodology to the Posterior Segment, American Journal of Ophthalmology, vol. 142, No. 5, Nov. 2006, pp. 777-787.e2.

Ozdamar et al. "Suprachoroidal seton implantation in refractory glaucoma: a novel surgical technique" J. Glaucoma Aug. 2003; 12(4):354-9.

Pinnas G. et al. "Cyclodialysis with teflon tube implants" Am J. Ophthalmol 1969 Nove; 68(5):879-883.

Portney GL, "Silicone elastomer implantation cyclodialysis." Arch Ophthalmol 1973; 89: 10-12.

Primary Open Angle Glaucoma. Preferred Practice Patterns, American Academy of Ophthalmology.http://one.aao.org/CE/PracticeGuidelines/PPP_Content.aspx?cid=a5a59e02-450b-4d50-8091-b2dd2lefl_ff2#references (Accessed Nov. 1, 2008).

Pruett et al., "The Fishmouth Phenomenon-II. Wedge Scleral Buckling" Arch Ophthal.; Oct. 1977; vol. 95:1782-1787.

Qadeer "Acrylic Gonio-Subconjunctival Plates in Glaucoma Surgery" Br J Ophthalmol. Jun. 1954; 38(6): 353-356.

Quigley HA, Vitale S. Models of open-angle glaucoma prevalence and incidence in the United States. Invest Ophthalmol Vis Sci 1997; 38:83-91.

Richards et al. "Artificial Drainage Tubes for Glaucoma" Am J Ophth 60:1965,405-408.

Ritch, et al., "Uveoscleral Outflow", The Glaucomas. St. Louis: Mosby, 1996; pp. 337-343.

Rohen, Johannes W., Anatomy of the Aqueous Outflow Channels, Glaucoma, vol. 1, Chapter 14, pp. 277-296, Edited by J.E. Cairns, Grune & Stratton, Harcourt Brace Jovanovich Publishers, 1986.

Rosenberg, et al. "Implants in glaucoma surgery" Chapter 88, The Glaucomas, Ritch et al. Eds. 2nd Ed. Mosby St. Louis 1996; p. 1783-1807.

Row H. "Operation to control glaucoma: preliminary report" Arch. Ophthal 12:325 (1934).

Rowan, Patrick J., MD, Combined Cyclodialysis and Cataract Surgery, Ophthalmic Surgery and Lasers, Dec. 1998, vol. 29, No. 12, pp. 962-968 (9 pages).

Sampimon "A New Approach to Filtering Glaucoma Surgery" Ophthalmologica (Basel) 151: 1966, 637-644.

Schappert S. Office visits for glaucoma: United States, 1991-92. Advance data from vital and health statistics. vol. 262. Hyattsville, MD: National Center for Health Statistics, 1995.

Schocket, Stanley S. "Investigations of the Reasons for Success and Failure in the Anterior Shunt-to-the-Encircling-Band Procedure in the Treatment of Refractory Glaucoma." *Tr. Am. Ophth. Soc.*vol. LXXXIX. (1986):743-798.

Shaffer RN, Weiss DI. Concerning cyclodialysis and hypotony. Arch Ophthalmol 68: 25, 1962.

SOLX Clinical Literature Handout; Industry Show Feb. 2006; "The SOLX Gold Micro-shunt (GMS) treatment".

Sommer A, Tielsch JM, Katz J, et al. Racial differences in the cause-specific prevalence of blindness in east Baltimore. N Engl J Med 1991;325:1412-7.

Sourdille et al. "Reticulated hyaluronic acid implant in non-perforating trabecular surgery." J Cataract Refract Surg 25: 332-339. (1999).

Spiegel et al. "Schlemm's Canal Implant: A New Method to Lower Intraocular Pressure in Patients With POAG?" *Ophthalmic Surgery and Lasers.* vol. 30, No. 6: 492-494, Jun. 1999.

Srinivasan et al. "Microbial contamination of the anterior chamber during phacoemulsification" J. Cataract Refract Surg. 28:2173-6 (2002).

Suguro K, Toris CB, Pederson JE. Uveoscleral outflow following cyclodialysis in the monkey eye using a fluorescent tracer. Invest Ophthalmol Vis Sci 1985: 26, 810.

The Advanced Glaucoma Intervention Study (AGIS): 7. The relationship between control of intraocular pressure and visual field deterioration. The AGIS Investigators. Am J Ophthalmol 2000;130:429-40.

The Advanced Glaucoma Intervention Study (AGIS); 13. Comparison of treatment outcomes within race: 10-year results. Ophthalmology 2004;111:651-64.

The Glaucoma Laser Trial (GLT) and Glaucoma Laser Trial Follow-up Study: 7. Results. Am J Ophthahnol 1995;120:718-31.

The Glaucoma Laser Trial (GLT). 2. Results of argon laser trabeculoplasty versus topical medicines. The Glaucoma Laser Trial Research Group. Ophthalmology 1990;97:1403-13.

Thiagalingam S, Tarongoy P, Hamrah P, Lobo AM, Nagao K, Barsam C, Bellows R, Pineda R. Complications of cosmetic iris implants. J Cataract Refract Surg. Jul. 2008;34(7):1222-4.

Tielsch JM, Sommer A, Katz J, et al. Racial variations in the prevalence of primary open-angle glaucoma. The Baltimore Eye Survey. JAMA 1991;266:369-74.

Toris CB. Extravascular albumin concentration of the uvea. Invest Ophthalmol Vis Sci 1990; 31:43.

Toris et al. "Aqueous humor dynamics in the aging human eye" Am J. Ophthalmol., 127:407-12 (1999).

Toris et al. "Effect of intraocular pressure on uveoscleral outflow following cyclodialysis in the monkey eye." Investigative Ophthalmology & Visual Science. 26 (1985) 1745-1749.

*Transcend Medical Inc.* v. *Glaukos Corporation*, Transcend Medical, Inc.'s Disclosures Pursuant to Default Discovery Rule 4 (d) (United States District Court for the District of Delaware, dated Dec. 6, 2013; case No. C.A. No. 13-830 (MSG) and Certificate of Service, dated Dec. 9, 2013.

Trigler L, Proia AD, Freedman SF. Fibrovascular ingrowth as a cause of Ahmed glaucoma valve failure in children. Am J Ophthalmol. Feb. 2006;141(2):388-9.

Troncoso Manuel U., "Cyclodialysis with insertion of metal implant in treatment of glaucoma, A Preliminary Report" Arch. Ophthal. 23:270 (1940).

Troncoso, Manuel U., Tantalum implants for inducing hypotny, Am Journal of Ophthalmology, vol. 32(4):499-508 (1949).

Van der Veen et al. "The gonioseton, a surgical treatment for chronic glaucoma". Documenta Ophthalmologica; vol. 75, Nos. 3-4, 365-375. (1990).

(56) References Cited

OTHER PUBLICATIONS

Vossmerbaeumer U, Ditzen K, Jonas JB. Removal of an intracorneal hydrogel implant for hyperopia after LASIK. J Refract Surg, Jan. 2007;23(1):102-4.

Wagner, Justin A., et al., Characterization of Uveoscleral Outflow in Enucleated Porcine Eyes Perfused under Constant Pressure, Invest Ophthalmol Vis Sci., Published in edited form in Sep. 2004, vol. 45, Issue 9, pp. 3203-3206.

Wamsley S, Master MR, Rai S, Alvim HS, Fontanarosa J. Results of the use of the Ex-PRESS miniature glaucoma implant in technically challenging, advanced glaucoma cases: a clinical pilot study. Am J Ophthalmol. Dec. 2004; 138(6): 1049-51.

Yablonski, "Some thoughts on the pressure dependence of uveoscleral flow" Journal of Glaucoma, 12(1):90-92 (2003).

Yablonski, "Trabeculectomy with Internal Tube Shunt: a novel glaucoma surgery" J. Glaucoma 14:91-97 (2005).

Yoo C, Kwon SW, Kim YY. Pericardium plug in the repair of the corneoscleral fistula after ahmed glaucoma valve explantation. Korean J Ophthalmol. Dec. 2008;22(4):268-71.

Zhou et al. "A trabecular bypass flow hypothesis" J Glaucoma. 14(1):74-83 (2005).

Haddrill, Marilyn. "Glaucoma Surgery." All About Vision.com. (2000). 6 pages. www.allaboutvision.com/conditions/glaucoma-surgery.htm. Accessed Aug. 23, 2017.

U.S. Appl. No. 14/254,366, filed Apr. 16, 2014, 2014-0309599.
U.S. Appl. No. 14/987,133, filed Jan. 14, 2016, 2016-0193083.
U.S. Appl. No. 15/165,759, filed May 26, 2016, 2016-0346125.
U.S. Appl. No. 15/268,305, filed Sep. 16, 2016, 2017-0079839.
PCT/US2016/052267, Sep. 16, 2016, WO 2017-051247.

\* cited by examiner

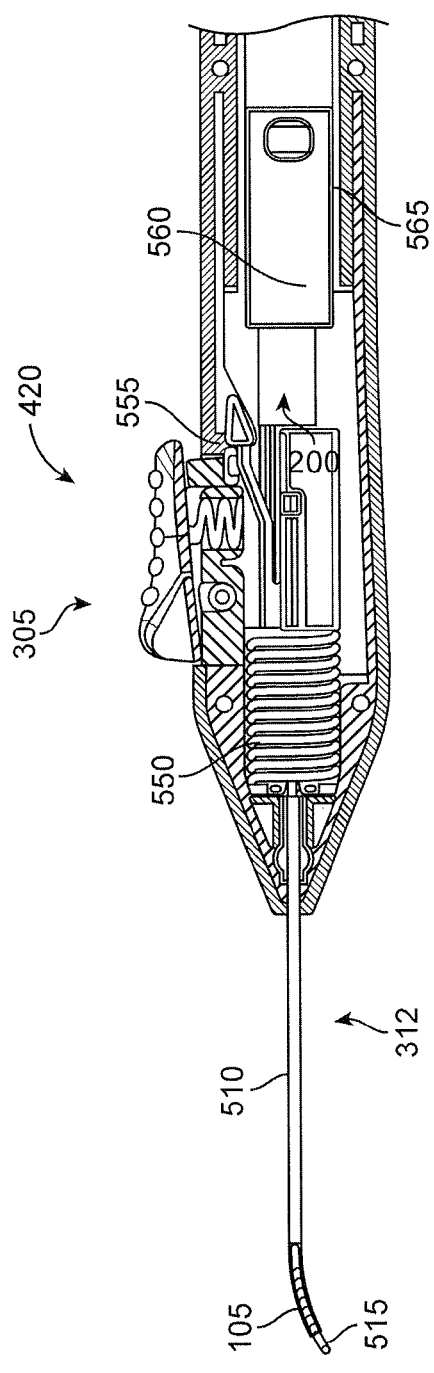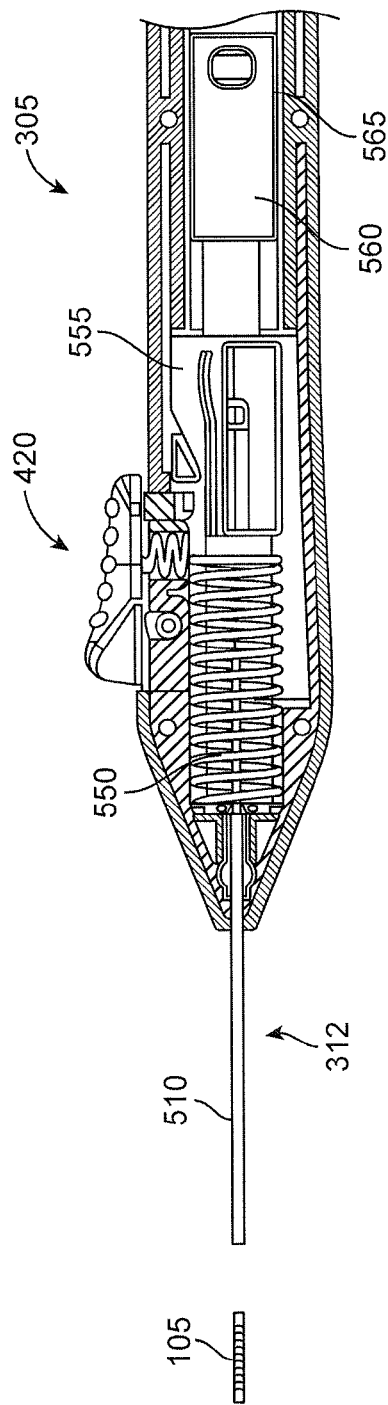
FIG. 5
FIG. 6

DELIVERY SYSTEM FOR OCULAR IMPLANT

REFERENCE TO PRIORITY DOCUMENT

This application is a continuation of U.S. patent application Ser. No. 14/176,918 entitled DELIVERY SYSTEM FOR OCULAR IMPLANT, filed Feb. 10, 2014, which is a continuation of U.S. patent application Ser. No. 13/865,947 entitled DELIVERY SYSTEM FOR OCULAR IMPLANT, filed Apr. 18, 2013, which claims priority benefit under 35 U.S.C. § 119(e) of U.S. Provisional Patent Application Ser. No. 61/637,789, filed Apr. 24, 2012 and entitled "Delivery System for Ocular Implant." The priority to the filing dates is hereby claimed and the disclosures of the patent applications are hereby incorporated by reference in their entirety.

BACKGROUND

This disclosure relates generally to methods and devices for use in delivering devices for treating glaucoma.

The mechanisms that cause glaucoma are not completely known. It is known that glaucoma results in abnormally high pressure in the eye, which leads to optic nerve damage. Over time, the increased pressure can cause damage to the optic nerve, which can lead to blindness. Treatment strategies have focused on keeping the intraocular pressure down in order to preserve as much vision as possible over the remainder of the patient's life.

Pursuant to such strategies, one or more implants can be delivered into the eye for shunting fluid out of the anterior chamber in order to regulate pressure in the eye. Accurate placement of an implant in the angle of the eye is critical for the targeted effect of reducing intraocular pressure (IOP). Placing an implant too distally into the eye, such as too distally into the supraciliary space, may leave no portion of the implant remaining in the anterior chamber. This may inhibit aqueous outflow, as the fluid will not have a direct communication with the flow target location if there is no opening to the anterior chamber.

Conversely if the implant is placed too proximally in the supraciliary space such that a significant portion of the implant remains in the anterior chamber, damage to the corneal endothelium may result from implants that protrude upwards and touch the cornea. Implants placed too proximally may also touch the iris resulting in increased amounts of pigment dispersion in the eye, which can increase outflow resistance and intraocular pressure by clogging the trabecular meshwork. Correct placement of the implant is desired for a safe and successful surgical outcome.

In view of the foregoing, there is a need for improved delivery systems for delivering implants into the eye such as by way of an ab interno procedure.

SUMMARY

There is a need for improved delivery systems, devices and methods for the treatment of eye diseases such as glaucoma.

In a first embodiment, disclosed herein is a delivery device for delivering an ocular implant into an eye. The delivery device can include a proximal handle portion and a distal delivery portion coupled to a distal end of the handle portion and configured to releasably hold an ocular implant. In addition, the delivery portion can include a sheath positioned axially over a guidewire. The delivery device can further include an actuator coupled to a mechanism that releases the ocular implant from the delivery portion upon actuation of the actuator.

Also described herein are methods of delivering an ocular implant to a target location within an eye. In an embodiment, disclosed is a method including loading the ocular implant onto a distal delivery portion of a delivery system. The delivery system can include a proximal handle portion with the delivery portion coupled to a distal end of the handle portion. In addition, the delivery portion can be configured to releasably hold the ocular implant. The delivery portion can further include a sheath positioned axially over a guidewire. Additionally, the delivery device can include an actuator coupled to a mechanism that releases the ocular implant from the delivery portion upon actuation of the actuator. The method can further include inserting the distal delivery portion and the ocular implant into the eye through a corneal incision and positioning the ocular implant into the target location within the eye by way of an ab-interno procedure. Furthermore, the method can include actuating the actuator and releasing the ocular implant into the target location.

Other features and advantages should be apparent from the following description of various embodiments, which illustrate, by way of example, the principles of the described subject matter.

BRIEF DESCRIPTION OF THE DRAWINGS

These and other aspects will now be described in detail with reference to the following drawings.

FIG. 5 shows a partial cross section view of the delivery system of FIG. 3 showing a distal portion of the handle component, including the spring-loaded actuator in a compressed configuration, and the distal delivery component.

FIG. 6 shows the partial cross section view of the delivery system of FIG. 5 with the spring-loaded actuator shown in a decompressed configuration which releases the implant from the distal delivery component.

Like reference symbols in the various drawings indicate like elements.

DETAILED DESCRIPTION

Figure 1:
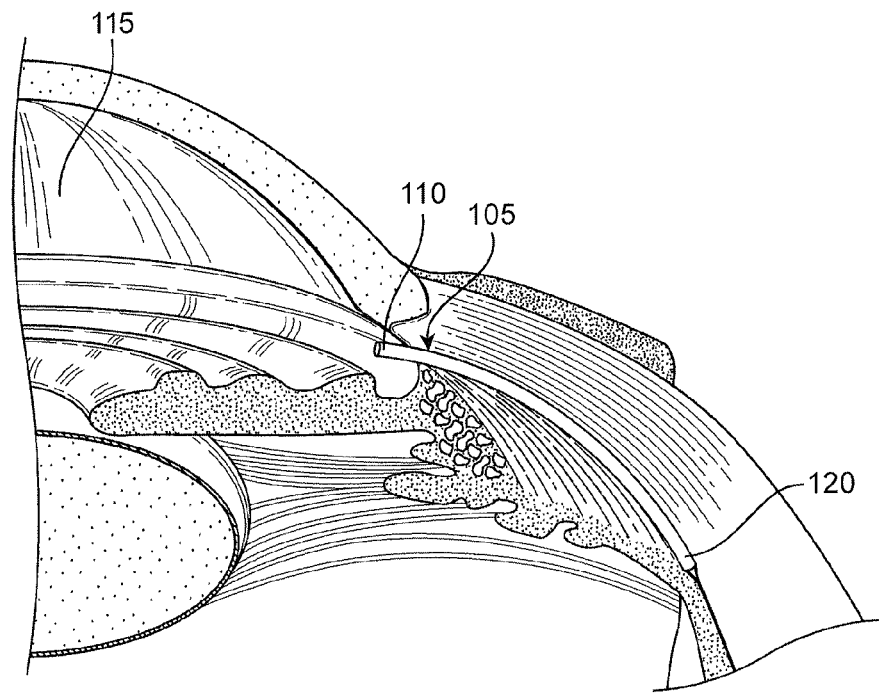
FIG. 1 shows an example cross-sectional view of a portion of the human eye.

FIG. 1 is a cross-sectional, perspective view of a portion of the eye showing the anterior and posterior chambers of the eye. A schematic representation of an implant 105 is positioned inside the eye such that a proximal end 110 is located in the anterior chamber 115 and a distal end 120 communicates with and/or is located in or near the supraciliary space or suprachoroidal space (sometimes referred to as the perichoroidal space). It should be appreciated that FIG. 1 and other figures herein are schematic and are not necessarily to scale with respect to size and relative positions of actual eye tissue.

The implant 105 provides a fluid pathway between the anterior chamber 115 into the supraciliary space and toward the suprachoroidal space. The implant 105 has a distal end 120 that may be positioned in the supraciliary space or the suprachoroidal space. The implant 105 may be positioned at least partially between the ciliary body and the sclera or it may be at least partially positioned between the sclera and the choroid. The distal end 120 of the implant 105 is not necessarily positioned between the choroid and the sclera.

In an embodiment, the implant 105 is an elongate element having one or more internal lumens through which aqueous humor can flow from the anterior chamber 115 into the supraciliary space. The implant 105 can have a substantially uniform internal diameter along its entire length, although the shape of the implant 105 can vary along its length (either before or after insertion of the implant), as described below. Moreover, the implant 105 can have various cross-sectional shapes (such as a circular, oval or rectangular shape) and can vary in cross-sectional shape moving along its length. The cross-sectional shape can be selected to facilitate easy insertion into the eye. The following applications describe exemplary implants: U.S. Patent Publication Nos. 2007-0191863 and 2009-0182421. These applications are incorporated by reference in their entirety.

Figure 2:
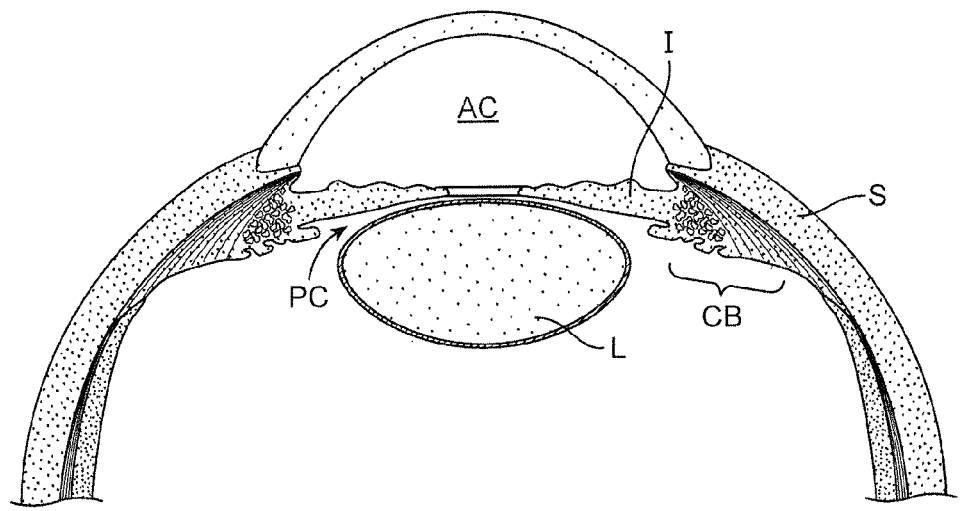
FIG. 2 shows and an example partial cross-sectional view of the eye showing a part of the anterior and posterior chambers of the eye and an ocular implant implanted in the eye.

FIG. 2 is a cross-sectional view of a portion of the human eye. The eye is generally spherical and is covered on the outside by the sclera S. The retina (not shown) lines the inside posterior half of the eye. The retina registers the light and sends signals to the brain via the optic nerve. The bulk of the eye is filled and supported by the vitreous body, a clear, jelly-like substance. The elastic lens L is located near the front of the eye. The lens L provides adjustment of focus and is suspended within a capsular bag from the ciliary body CB, which contains the muscles that change the focal length of the lens. A volume in front of the lens L is divided into two by the iris I, which controls the aperture of the lens and the amount of light striking the retina. The pupil is a hole in the center of the iris I through which light passes. The volume between the iris I and the lens L is the posterior chamber PC. The volume between the iris I and the cornea is the anterior chamber AC. Both chambers are filled with a clear liquid known as aqueous humor.

The ciliary body CB continuously forms aqueous humor in the posterior chamber PC by secretion from the blood vessels. The aqueous humor flows around the lens L and iris I into the anterior chamber and exits the eye through the trabecular meshwork, a sieve-like structure situated at the corner of the iris I and the wall of the eye (the corner is known as the iridocorneal angle). Some of the aqueous humor filters through the trabecular meshwork near the iris root into Schlemm's canal, a small channel that drains into the ocular veins. A smaller portion rejoins the venous circulation after passing through the ciliary body and eventually through the sclera (the uveoscleral route).

The internal lumen of the implant 105 serves as a passageway for the flow of aqueous humor through the implant 105 directly from the anterior chamber toward or into the supraciliary or suprachoroidal space. In addition, the internal lumen of the implant 105 can be used as an access location to mount the implant 105 onto a delivery device, as described in more detail below. The internal lumen can also be used as a pathway for flowing fluid, such as an irrigation fluid or a visco-elastic substance(s), into the eye for flushing or to maintain pressure in the anterior chamber, or using the fluid to assist in dissection, visualization or hydraulic creation of a dissection plane into or within the suprachoroidal space.

Fluid can be flowed toward or into the supraciliary or suprachoroidal space, for example via a delivery cannula or through the internal lumen of the shunt. The fluid can be flowed into the eye with a pressure sufficient to form a dissection plane into or within the supraciliary suprachoroidal space. The fluid can accumulate within the eye so as to form a lake. In general, hydro-dissection or the injection of fluids such as a visco-elastic substance(s) can be used to separate the ciliary body from the sclera to enlarge an area of detachment of the ciliary body from the sclera with or without insertion of a device.

Figure 3:
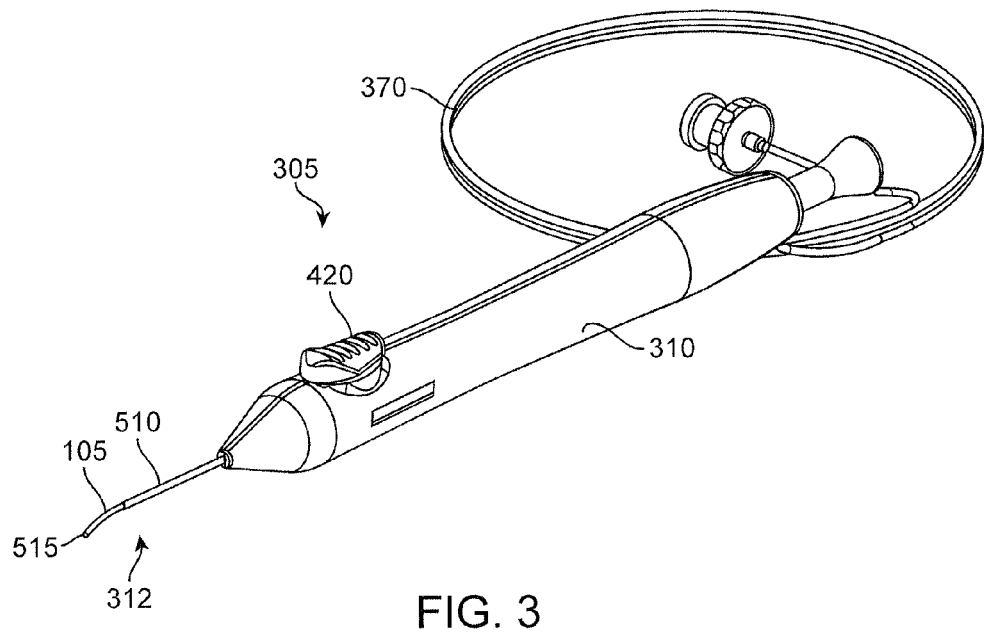
FIG. 3 shows a perspective view of an embodiment of a delivery device having a proximal handle component and a distal delivery component with an ocular implant loaded onto the distal delivery component.

FIG. 3 shows an embodiment of a delivery system 305 that can be used to deliver the implant 105 into the eye. In some embodiments, the implant 105 can provide fluid communication between the anterior chamber toward the suprachoroidal or supraciliary space while in an implanted state. It should be appreciated that these delivery systems 305 are exemplary and that variations in the structure, shape and actuation of the delivery system 305 are possible. The delivery system 305 can include a proximal handle component 310 and a distal delivery component 312. The proximal handle component 310 can include an actuator 420, such as a button, to control the release of an implant from the delivery component 312 into a target location in the eye. The actuator 420 can vary in structure and is not limited to a button.

An embodiment of the delivery component 312 includes an elongate applier in the form of a guidewire 515 and a "stopper" or sheath 510 positioned axially over the guidewire 515. The guidewire 515 can insert longitudinally through the internal lumen of the implant 105 and can assist in inserting and positioning the implant 105 into the target location. The sheath 510 can aid in the release of the implant 105 from the delivery component 312 into the target location in the eye. In addition, the actuator 420 can be used to control movement or relative movement of the guidewire 515 and/or the sheath 510. For example, the sheath 510 can be fixed relative to the handle component 310 and act as a stopper which can impede the implant 105 from moving in a proximal direction as the guidewire 515 is withdrawn proximally from the implant 105 upon actuation of the actuator 420.

For example, in a first state, the guidewire 515 can be extended distally relative to a distal end of the sheath 510. Actuation of the actuator 420, such as by pressing the actuator 420, can cause the guidewire 515 to slide proximally or retract into the sheath 510. This can effectively disengage the implant 105 off the distal end of the guidewire 515 and releases the implant 105 in a controlled fashion into the target location. Controlled disengagement of the implant 105 off the distal end of the guidewire 515 can assist in ensuring that positioning of the implant 105 within the target location is maintained.

Figure 4:
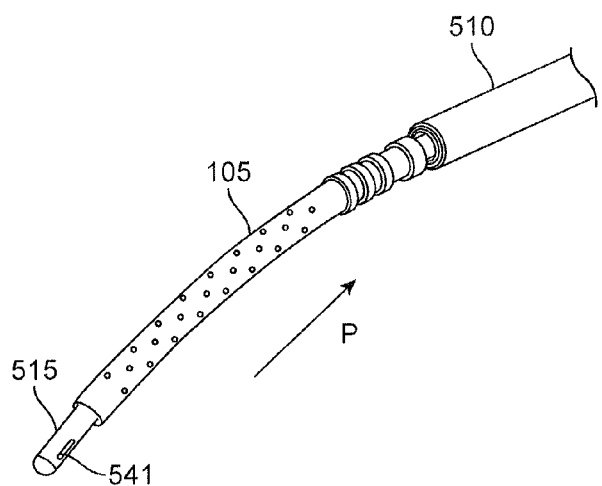
FIG. 4 shows a close up view of the distal end of the delivery component of FIG. 3 which illustrates the implant loaded onto a guidewire of the delivery system.

FIG. 4 shows an embodiment of the implant 105 mounted on the delivery component 312 of the delivery system 305. More specifically, the implant 105 can be mounted on the distal region of the guidewire 515, as shown in FIG. 4. In addition, the sheath 510 can be sized and shaped to receive or abut a portion of the proximal end of the implant 105. In this embodiment, upon actuation of the actuator 420, the guidewire 515 can slide in a proximal direction (arrow P) into the sheath 510 which can allow the proximal end of the implant 105 to abut the distal end of the sheath 510 and prevent the implant 105 from sliding in the proximal direction. This can effectively disengage the implant 105 off the distal end of the guidewire 515 and controllably releases the implant 105 into the target location within the eye.

In some embodiments, the actuator 420 can be a push-button that is coupled to a spring-activated mechanism. Upon applying a force onto the actuator 420, the spring mechanism can retract the guidewire 515 toward and/or into the sheath 510 which can release the implant 105 from the guidewire 515. The mechanism by which the guidewire 515 can be withdrawn into the sheath 510 can be a spring activated assembly or any of a variety of mechanisms that allow the guidewire to retract upon activation of an actuator.

FIG. 5 shows an embodiment of a portion of the delivery system 305 in cross-section with the implant 105 loaded onto the guidewire 515. The delivery system 305 can include a front spring 550 which can assist in positioning the guidewire 515. For example, the front spring 550 can be compressed or charged which can allow the guidewire 515 to be positioned in an extended state relative to the handle 310. When the guidewire 515 is in an extended state, the guidewire 515 can be loaded with the implant 105, as shown in FIG. 5.

The delivery system 305 can include a variety of mechanisms for assisting in the positioning of the guidewire 515. For example, the delivery system 305 can include a feature which can interact with the actuator 420 in order to allow the actuator to assist in positioning the guidewire 515. For example, the guidewire 515 can be attached at a proximal end to a piston 560 having a de-tent latch 555. The de-tent latch 555 can interact with the actuator 420 such that upon actuation of the actuator 420, the 555 latch can release the piston 560 from a locked position and allow the piston 560 to move. For example, once the piston 560 is allowed to move, the front spring 550 can force the piston to move in a direction, such as in a proximal direction, thus causing the guidewire 515 to move in a proximal direction. Movement of the guidewire 515 in a proximal direction can allow the implant 105 loaded on the distal end of the guidewire 515 to be released from the guidewire 515.

In some embodiments, the actuator 420 can be configured such that when actuated or depressed by the user, the detent latch 555 of the piston 560 is flexed downward thereby allowing the front spring 550 to release. As the piston 560 moves proximally with the guidewire 515, the implant 105 can abut the distal end of the stopper tube 510 and release from the guidewire 515. FIG. 6 shows an embodiment of the delivery system 305 in a retracted state where the front spring 550 is in a decompressed state with the implant 105 fully released from the guidewire 515.

The travel of the piston 560 can be defined such that the guidewire 515 reaches a complete stop in the proximal direction only after the implant 105 is fully released. In addition, the force of the front spring 550 can allow withdrawal of the guidewire 515 from the implant 105 when the implant 105 is positioned in a variety of angles relative to the stopper tube 510. For example, the force of the front spring 550 can allow the withdrawal of the guidewire 515 from the implant 105 when the implant 105 is at a 45 degree angle relative to the stopper tube 510, such as what may be encountered when the implant 105 is being deployed to the supraciliary space.

In some embodiments, for example, the front spring 550 can provide approximately 1.0 to 2.0 lbf at the compressed or charged configuration which can allow the guidewire 515 to withdraw from the implant 105, including when the implant 105 is positioned at an approximate 45 degree angle relative to the stopper tube 510. However, the front spring 550 can provide any of a variety of spring force which allows the guidewire 515 to release the implant 105 positioned at a variety of angles relative to at least the stopper tube 510.

In some embodiments, the front spring 550 can create approximately 2.0 to 10.0 lbf. For example, a greater spring force of the front spring 550 can allow the guidewire 515 to retract in a variety of conditions. In addition, a lower force of the front spring, such as 0.10 to 1.0 lbf, may reduce the speed of the retraction and reduce the force required to reload the system. Any of a variety of front springs 550 can be implemented in the delivery system 350.

A dampening element, such as grease 565, may be placed between the piston 560 and inside wall of the handle 310 which can assist in providing a slower retraction of the guidewire 515. A slower retraction of the guidewire 515 can prevent or lessen any jerking motion of the delivery system 350 in the user's hands, including at the end of the piston 560 travel. This dampening grease 565 can be a silicone grease such that grease is unaffected by production level e-beam sterilization dose of 25-50 kGy. In addition, other dampening elements aside from grease 565 may be used. Alternate dampening grease such as low, medium, or high viscosity fluorocarbons may be used to alter the dampening and speed of deployment. These materials may have a larger acceptable e-beam sterilization range.

In some embodiments, the spring-activated retraction of the guidewire 515 can improve the delivery of supraciliary and suprachoroidal implants. For example, some current tools for implanting ocular implants require a sliding motion of the user's finger, such as in the range of approximately 0.280" inches of travel, in order to release the implant. The sliding motion can be difficult for surgeons to achieve while simultaneously holding the distal end of the delivery tool steady. In contrast, the spring-activated mechanism of the present disclosure, including the spring activated push-button mechanism, allows for smaller and more ergonomic motion of the users finger to activate guidewire 515 retraction which also allows the user to maintain the distal end of the delivery device 312 in a steady position. In addition, the spring-activated mechanism of the present disclosure can allow implantation to occur more quickly and with less unwanted distal movement of the implant 105 during the guidewire retention.

The outer diameter of the guidewire 515 can be smaller than the inner diameter of the implant 105 (i.e. the fluid channel) such that the implant 105 can be loaded onto the guidewire 515 by sliding the guidewire 515 into and through an internal lumen of the implant 105. In some embodiments, the guidewire 515 can include a retention feature that can act to retain the implant 105 on the guidewire 515. For example, the guidewire 515 can include a retention feature which can assist in retaining the implant 105 on the guidewire 515 during blunt dissection and implantation in order to prevent the implant 105 from inadvertently sliding off the guidewire 515.

Before the implant 105 has been released from the guidewire 515 and implanted into the target location within the eye, the implant 105 can be moved either distally or proximally in order to adjust its placement. This can exert axial forces on the implant 105 which may cause it to slip off the guidewire 515 if it is not well retained on the guidewire 515. Therefore, in some embodiments, the guidewire 515 can include features which can assist in retaining the implant 105 onto the guidewire 515 during positioning of the implant 105, including positioning the implant 105 within the target location.

Figure 7:
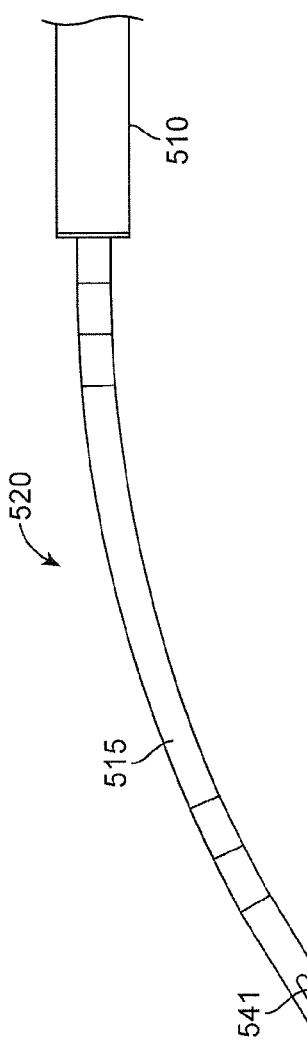
FIG. 7 shows an embodiment of the guidewire of the delivery system having a curved configuration.

FIG. 7 shows an embodiment of a guidewire 515 which has at least one retention feature including a curved configuration 520 along a length of the guidewire 515. In some embodiments, the curved configuration 520 of the guidewire 515 can assist in facilitating entry of the implant 105 into the supracilliary space. In addition, the curvature of the guidewire 515 can change the shape of the implant 105 due to the implant 105 conforming to the curved shape of the guidewire 515 which can facilitate placement of the implant 105 into the supraciliary space as it curves along the scleral wall. The curvature radius or arc, including the curved configuration 520 of the guidewire 515, can vary and can be in the range of approximately 0.425" to about 0.525" with a central angle of approximately 20 degrees to approximately 40 degrees.

Additionally, any part of the guidewire 515 can have the curved configuration 520, including either the distal end or the entire length of the guidewire 515. Furthermore, the guidewire 515 can alternate between having a variety of configurations, including both straight and curved configurations. For example, the guidewire 515 can have a curved configuration in its natural state but can conform to a straight passageway, such as through the handle 310 of the delivery system 305. Therefore, the guidewire 515 can conform to a straight passageway and return to a curved configuration after having passed through the straight passageway.

In some embodiments, the guidewire 515 can have one or more cut patters along a length of the guidewire 515 which can allow the guidewire 515 to be more flexible than the material comprising the guidewire 515 can allow. For example, the distal end or tip of the guidewire 515 can include a spiral cut pattern which allows the tip of the guidewire 515 to deflect or bend in one or more of a variety of directions relative to a longitudinal axis of the guidewire 515. Furthermore, the spiral cut pattern can allow the distal end or tip of the guidewire 515 to deflect or bend to a greater degree than what the guidewire could achieve without the spiral cut pattern. These cut patterns may additionally serve as fluid conduits which can provide a passageway for substances injected into the guidewire 515 to be released to an area surrounding the guidewire, including either the implant or the eye.

Figure 8:
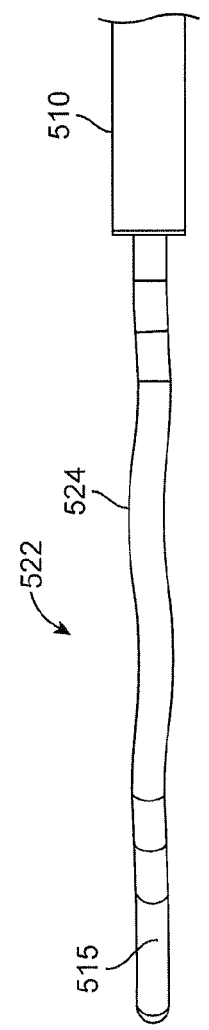
FIG. 8 shows an embodiment of the guidewire of the delivery system having a sinusoidal configuration.

FIG. 8 shows an embodiment of the guidewire 515 having at least one retention feature including a sinusoidal or S-curve configuration along a length of the guidewire 515. The sinusoidal or S-curve configuration can assist in retaining the implant 105 onto the guidewire 515, such as by at least one curved region 524 along a length of the guidewire 515. The at least one curved feature can include a protrusion, bump, etc. For example, the curved feature 524 can be configured to provide an interference fit between the guidewire 515 and the inner lumen of the implant 105.

In some embodiments, the retention feature can include an S-shaped curve along a length of the guidewire 515 which can have one or more rounded curved features 524, including bends or peaks, as shown in FIG. 8. Furthermore, each retention feature, such as curved feature 524, can form a point of contact between the inner lumen of the implant 105 and the guidewire 515. The curved features 524 of the guidewire S-curve can also reduce the risk of damaging the inner lumen of the implant 105 as the guidewire 515 is released from the implant 105. In addition, the retention features can provide a gentle interaction and retention between the guidewire 515 and the implant 105, including during removal of the guidewire 515 from the implant 105. Alternatively, the guidewire 515 retention features can be stamped, bent or shape-set, including in the shape of swells or other formations along at least a part of the length of the guidewire 515.

In an embodiment, an amount of retention force can be defined by the peak-to-peak distance between two or more retention features or curved features 524 of the implant 105. For example, larger peak-to-peak distances between the two or more curved features 524 can produce higher retention forces and smaller peak-to-peak distances can produce lower retention forces. In some embodiments, a peak-to-peak distance that is too large can cause damage to the implant 105, such as due to the guidewire 515 scraping away material along the inner lumen during removal. For example, the peak-to-peak distance may be in the range of approximately 0.0100" to approximately 0.0200", or in the range of approximately 0.0120" to approximately 0.0150". In addition, at least one retention force acting upon the implant 105, such as a polyimide implant, by the guidewire 515 of approximately 0.050-0.200 lbf can be sufficient to retain the implant 105 along the guidewire 515 during manipulation of the implant 105 prior to implantation into the target location.

In alternate embodiments, the material of the guidewire 515 can be made out of one or more flexible materials, such as metals including stainless steel or elgiloy, and polymers such as Pebax, silicones, urethanes, including a variety of combinations of materials. In some embodiments, the guidewire 515 can have a radius of curvature or arc which is less than 0.425", such as in order to provide a small curvature of the implant 105 during insertion. This configuration can be advantageous when access between the incision and the target location requires the implant 105 to be introduced into the target location by way of a small radius, such as less than 0.425".

Alternatively, the radius of curvature or arc of the guidewire 515 can be larger than 0.525". Any of a variety of radius of curvature or arcs of the guidewire 515 can be implemented into any of the delivery systems 305 in order to best accommodate insertion of the implant 105 into the designated target location. For example, the radius of curvature or arc of the guidewire 515 may be such that it can allow the implant 105 to bend against the scleral wall during insertion into the supraciliary space. In addition, the retention features of the guidewire 515 can vary and can include one or more of a variety of shapes and sizes along a length of the guidewire 515. For example, the retention features can be configured to include spiral shapes, triangle peaks or the like. Additionally, the retention features can extend along one or more of a variety of planes, including more than one retention feature extending in planes positioned perpendicular relative to each other.

In addition, any number of retention features can be positioned along a length of the guidewire 515. For example, at least two, including more than five or more than ten retention features can be positioned along a length of the guidewire 515. In addition, each retention feature can provide the same or a variety of different amounts of retention forces for securing the implant 105 in a position along the guidewire 515. In some embodiments, the peak-to-peak distance between the retention features can be larger than the inner diameter of the implant 105 and can be a dimensioned larger than 0.0150" such that it does not damage the implant 105.

In some embodiments of the delivery system 305, instead of using the guidewire 515 to provide retention of the implant 105, an additional feature of the delivery system 305 or device can be used in order to provide the necessary retention of the implant 105 onto the guidewire 515. This may include, for example, a Pebax material which can be coupled onto a part of the guidewire 515 in order to create at least a width along the guidewire 515 that is larger than the inner diameter of the implant 105. For example, the Pebax material can be crimped to the guidewire and can retain the implant 105 relative to the guidewire 515 until the implant 150 is released from the delivery system 305, such as after actuation of the actuator 420.

As shown in FIGS. 3 and 4, the delivery system 305 can include at least one fluid delivery feature which can be configured to deliver fluid into at least one of the implant or the eye, including during or after implantation of the implant 105. The delivered fluid can vary and may include a viscoelastic, drugs, stem cells, or a combination thereof. In addition, the delivery may be in combination with retinal or macula therapy.

The at least one fluid delivery feature can include an elongated tube 370 having at least one inner lumen. The elongated tube 370 can extend outward from the handle 310. In addition, the elongated tube 370 can extend through the handle 310. Additionally, the elongated tube 370 can have an internal lumen which communicates with an internal lumen of the guidewire 515.

In some embodiments, the guidewire 515 can include one or more outlet openings, such as slots 541 (FIG. 4), which can be located along a length of the guidewire 515, including along a distal region of the guidewire 515. The slots 541 can allow fluid communication between the internal lumen of the guidewire 515 and an area surrounding the guidewire 515. In addition, the outlet openings or slots 541 can also be in fluid communication with at least one inner lumen of the elongated tube 370.

In some embodiments, the elongated tube 370 can be connected at a proximal end to a source of fluid (such as via a Luer connection). The source of fluid can provide fluid into at least one inner lumen of the elongated tube 370 which can be delivered to a variety of places either within at least one of the delivery system 305, the implant 105 or the eye. For example, some of the fluid provided by the fluid source can be passed through the elongated tube 370 and exit the guidewire 515 via the slots 541 for delivery into the eye.

The size of the at least one inner lumens of the elongated tube 370 and guidewire 515 may vary. In an embodiment, the inner lumen of either the elongated tube 370 or guidewire 515 can be within a range of approximately 0.001" to approximately 0.010" in diameter, or approximately 0.005" to approximately 0.009" in diameter. In addition, the size of the inner lumen can depend on the size constraints of the outer diameter of either the elongated tube 370 or the guidewire 515.

In some embodiments, the distal slots 541 of the guidewire 515 can allow fluid from at least the fluid source to be delivered to a distal end of the implant 105, including during or after implantation of the implant 105. In addition, fluid from the fluid source can be delivered to an area adjacent the distal end of the implant in order to create an aqueous lake or create a tenting effect around at least a part of or adjacent the implant 105. The size and location of the slots 541 can be sized, shaped and positioned along the guidewire 515 in order to create a variety of fluid delivery effects. For example, at least two slots 541 can be configured symmetrically relative to the distal end of the guidewire 515 which can allow the fluid to be delivered symmetrically around or near the distal end of the implant.

In an embodiment, the flow rate of the fluid from the fluid source can be within a range of approximately 1 mg/sec to 10 mg/sec, or approximately 2 mg/sec to 5 mg/sec. In addition, the burst pressure of the delivery system 305, including the fluid delivery features, can be large enough to withstand the pressure of injecting a fluid through the lumens of the delivery system 305 and implants 105.

In some embodiments, the burst pressure of the delivery system 305 can be larger than the pressure required for the fluid to flow from the fluid source through at least the delivery system 305. For example, the burst pressure can be approximately 400 psi to approximately 1500 psi, or approximately 600 psi to approximately 1200 psi. In addition, the burst pressure required for viscoelastic flow of Healon 5 can be approximately 100 psi to approximately 500 psi, or approximately 200 psi to approximately 300 psi.

In some embodiments, fluid from the fluid source can be delivered to one or more sections along the axial length of the implant 105. For example, one or more holes along the length of the implant 105 (as shown in FIG. 4) can be configured to be sufficiently large such that a fluid may be delivered from the guidewire 515. For example, one or more slits 514 positioned along the length of the guidewire 515, such as below a loaded implant 105, can allow fluid to travel through the at least one hole along the length of the implant 105 and into the eye. For example, the fluid can flow out from the one or more holes along the length of the implant and into the supraciliary or suprachoroidal space surrounding the body of the implant 105 (depending on where the implant is positioned and the length of the implant). The release of fluid through the at least one hole along the length of the implant 105 can assist in creating additional space surrounding the implant 105 which can improve tenting.

One or more drugs can be delivered to the inner lumen of the implant 105 through the one or more holes or slits 514 along the axial length of the guidewire 515. Alternatively or in addition, drugs can be delivered through the guidewire 515 slots 541 positioned at or near the distal end of the guidewire 515 which can dispense fluid either before or during retraction of the guidewire 515. In some instances, this can reduce the fibrotic response of the surrounding tissue to the implant 105. Additionally, the delivery of fluids may be administered through separate components that do not retain the implant 105. For example, separate tubes may be inserted into the eye alongside of the implant 105 which can deliver drugs or viscoelastic to, for example, the distal end of the implant 105.

Figure 9:
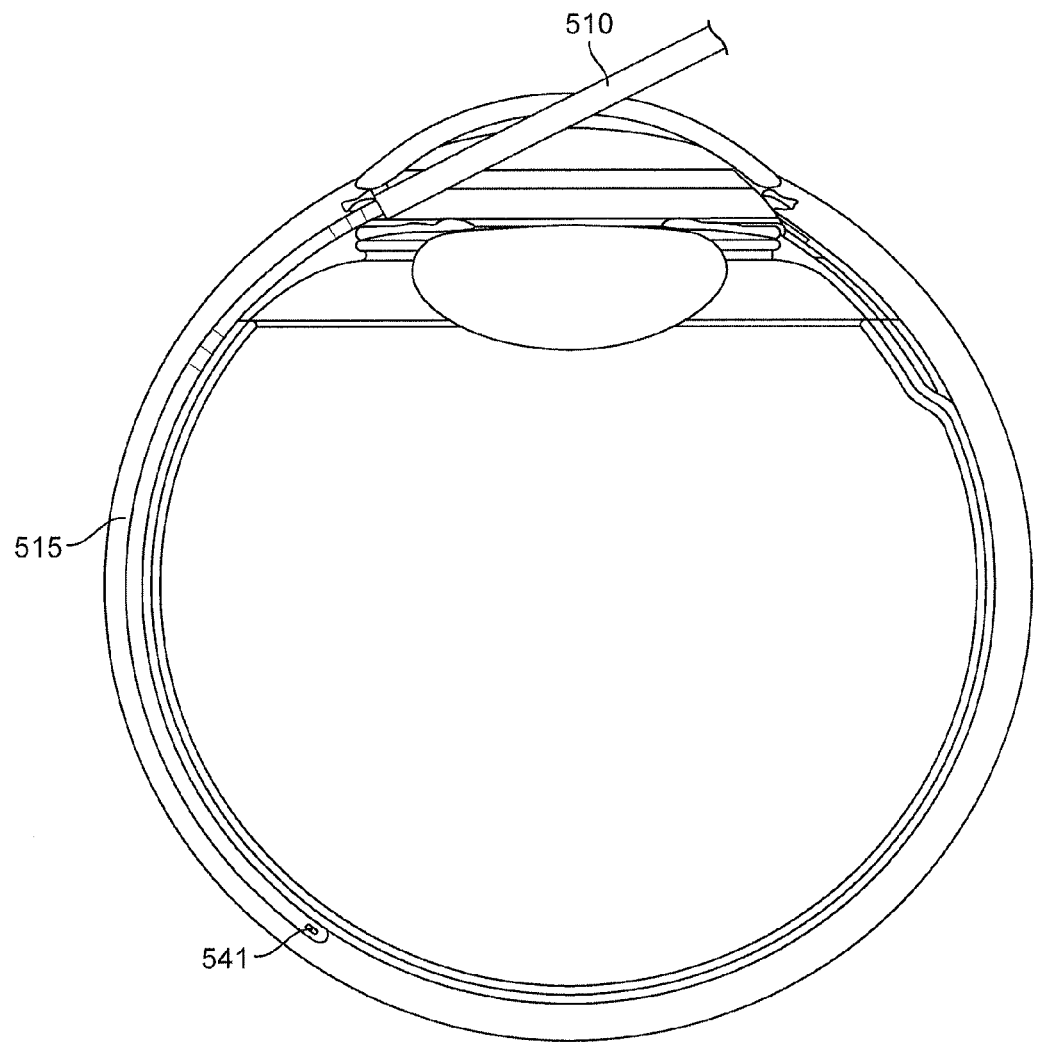
FIG. 9 shows an embodiment of the guidewire of the delivery system having a length sufficient to extend from the supraciliary space down to the sub-retinal space.

The system may also be used for the ab-interno delivery of fluids to other locations in the eye. FIG. 9, for example, shows the guidewire 515 having a length sufficient to extend from the supraciliary space down to the sub-retinal space. Fluid delivery in the subretinal portion of the eye may be advantageous because it can allow for direct delivery of drugs to the macula for diseases such as age related macular degeneration (AMD) or diabetic retinopathy, or the like. A variety of drugs can be delivered to the sub-retinal space, including anti-VEGF treatments or the like. Alternatively other fluids containing a stem cell therapeutic may be delivered through the guidewire 515 and into the sub-retinal or sub-macula space. These could be used to treat disease such as glaucoma, AMD, and diabetic retinopathy.

Additionally, fluid may be delivered to various anatomical structures comprising the eye. For example, fluid can be delivered to anatomical structures such as the Schlemm's Canal. By way of further example, the guidewire 515 can be passed through the Trabecular Meshwork, such as via an ab interno procedure, and into the Schlemm's Canal where viscoelastic substances can then be injected. The viscoelastic substances can then travel circumferentially around the eye for a number of hours which can dilate the Schlemm's Canal. In another embodiment, the guidewire 515 may be inserted through the sclera with the tip of the guidewire 515 just below the conjunctiva. Fluids such as viscoelastic may then be injected to create a sub-conjunctiva space which can form a filtration bleb.

A guidewire 515 assembly having an increased stiffness, such as one made from Nitinol, can be appropriately sized and delivered through an ab-interno approach. Alternate materials such as flexible polymers including Pebax, silicone, and urethane, can also be used. The ab-interno procedure can offer a patient significant reductions in complications and risks that are associated with the current ab-externo procedures, including conjunctivitis.

An example method of delivering and implanting the ocular implant 105 in the eye can include loading one or more implants 105 on a delivery system 305 and implanting the implants 105 by way of an ab interno procedure. The implant 105 can be implanted such that it can provide fluid communication between the anterior chamber and the supraciliary or suprachoroidal space. The implant 105 can then be secured in the eye so that it provides permanent fluid communication between the anterior chamber and the supraciliary space or suprachoroidal space.

The guidewire 515 can be positioned on the delivery system 305 such that the distal tip of the guidewire 515, the implant 105 and sheath 510 can penetrate through a small corneal incision in order to access the anterior chamber, such as along the limbus of the cornea. In an embodiment, the incision can be very close to the limbus, such as either at the level of the limbus or within 2 mm of the limbus in the clear cornea. The guidewire 515 can be used to make the incision or a separate cutting device can be used. For example, a knife-tipped device or diamond knife can be used to initially enter the cornea.

The corneal incision can have a size that is sufficient to permit passage of at least the implant 105. In an embodiment, the incision can be approximately 1 mm in size. In another embodiment, the incision can be no greater than approximately 2.85 mm in size. In another embodiment, the incision is no greater than approximately 2.85 mm and can be greater than approximately 1.5 mm.

After insertion through the incision, the guidewire 515 can be advanced into the anterior chamber along a pathway that enables the implant 105 to be delivered to a position such that the implant 105 provides a flow passageway from the anterior chamber toward the suprachoroidal space. The guidewire 515 can be advanced further into the eye such that the blunt distal tip of the guidewire 515 and/or the implant 105 seats with and can penetrate the iris root IR or a region of the ciliary body CB or the iris root part of the ciliary body near its tissue border with the scleral spur.

The guidewire 515 can approach the iris root from the same side of the anterior chamber as the deployment location such that the guidewire 515 does not have to be advanced across the iris. Alternately, the guidewire 515 can approach the location from across the anterior chamber such that the guidewire 515 is advanced across the iris and/or the anterior chamber toward the opposite iris root. The guidewire 515 can approach the eye and the iris root along a variety of pathways. For example, the guidewire 515 can be advanced through the anterior chamber such that it does not intersect the optical axis of the eye. In other words, the corneal incision and the location where the implant 105 is implanted at the iris root can be in the same quadrant (if the eye is viewed from the front and divided into four quadrants).

Figure 10:
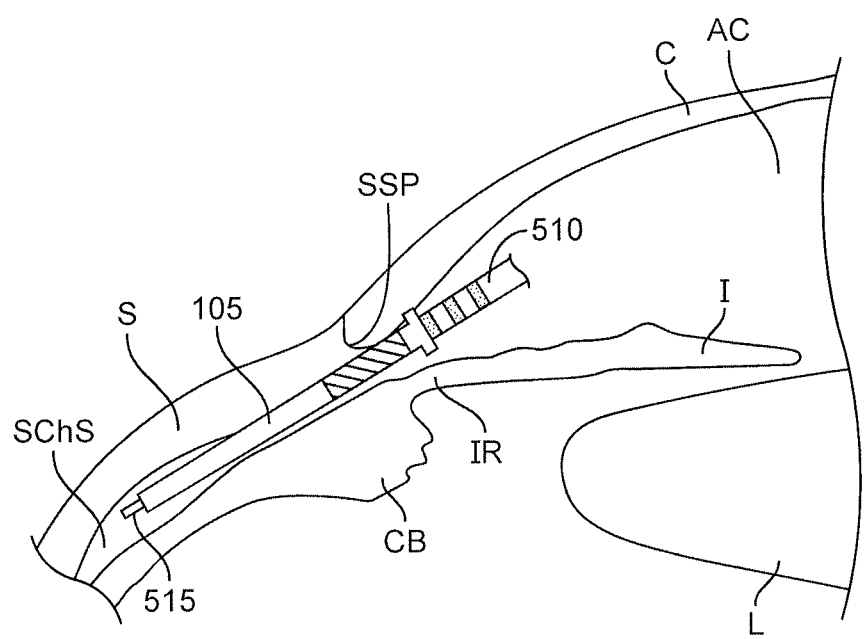
FIG. 10 shows an enlarged view of the anterior region of the eye with the implant approaching the supraciliary space or suprachoroidal space from the anterior chamber.

FIG. 10 shows an enlarged view of the anterior region of the eye showing the anterior chamber AC, the cornea C, the iris I, and the sclera S. In addition, FIG. 10 shows the implant 105 loaded onto a guidewire 515 and approaching the supraciliary space or suprachoroidal space from the anterior chamber AC. The implant 105 mounted on the guidewire 515 can move along a pathway such that the dissection entry point of the distal tip of the guidewire 515 can penetrate the iris root IR near its junction with the scleral spur SSp or the iris root portion of the ciliary body CB or other desired location. The surgeon can rotate or reposition the handle 310 of the delivery system 305 in order to obtain a proper approach trajectory for the distal tip of the guidewire 515, as described in further detail below.

The guidewire 515 with the implant 105 positioned thereupon can be advanced from a region of the anterior chamber which can be viewed through a transparent zone of the cornea to a region of the anterior chamber that may be obscured by an opaque zone of the cornea. The guidewire 515 and implant 105 can be advanced through the cornea C until resistance is felt and the delivery device can be seated at a location near the iris root IR, the ciliary body or the iris root portion of the ciliary body. The guidewire 515 can then be advanced further such that the guidewire 515 and implant 105 loaded thereon can penetrate an area of fibrous attachment between the scleral spur SSP and the ciliary body CB. This area of fibrous attachment can be approximately 1 mm in length. Once the distal tip of the guidewire 515 penetrates and is urged past this fibrous attachment region, the guidewire 515 can then more easily cause the sclera S to peel away or otherwise separate from the ciliary body CB and possibly the choroid as the guidewire 515 follows the inner curve of the sclera S and enters the supraciliary space. A combination of the guidewire's tip shape, material, material properties, diameter, flexibility, compliance, coatings, precurvature etc. can make it more inclined to follow an implantation pathway which mirrors the curvature of the inner wall of the sclera and between tissue layers such as between the sclera and the ciliary body, and between the sclera and the choroid.

The dissection plane of the guidewire 515 and implant 105 can follow the curve of the inner scleral wall such that the implant 105 mounted on the guidewire 515 can bluntly dissect the boundary between the scleral spur SSp and the ciliary body CB such that a distal region of the implant extends into the supraciliary space. For example, the dissection plane can be formed by the guidewire 515 and implant 105 after either the guidewire 515 or implant 105 penetrates the iris root or the iris root portion of the ciliary body. In an embodiment, the implant 105 can be positioned such that it does not extend anteriorly past the scleral spur SSP far enough to reach or otherwise contact the choroid. In addition, in some embodiments, the distal end of the implant 105 does not reach and cannot contact the choroid. In another embodiment, the implant 105 can extend sufficiently past the scleral spur SSP such that it can be positioned between the tissue boundaries of the sclera and the choroid (the suprachoroidal space).

In some embodiments, at least approximately 1 mm to approximately 2 mm of the implant (along the length) remains in the anterior chamber AC. The implant 105 can be positioned so that a portion of the implant 105 is sitting on top of the ciliary body CB. The ciliary body CB may act as a platform off of which the implant 105 can cantilever towards or into the suprachoroidal space SChS although the implant may not actually enter the suprachoroidal space. The implant 105 can lift or "tent" the sclera S outward such that a tented chamber is formed around the distal end of the implant 105. It should be appreciated that the actual contour of the tented region of tissue may differ in the actual anatomy. In some embodiments, the distal end of the implant 105 does not extend far enough to reach the choroid. In another embodiment, the distal end of the implant 105 reaches the choroid and can contact the choroid.

Once properly positioned, the implant 105 can then be released from the guidewire 515. The implant 105 can be released for example by withdrawing the guidewire 515 such that the implant 105 is effectively disengaged in a controlled manner from the tip of the guidewire 515 with the assistance of the sheath 510, as described above.

The implant 105 can include one or more structural features near its proximal region that aid to anchor or retain the implant 105 in the target location in the eye. The structural features can include flanges, protrusions, wings, tines, or prongs, and the like which can lodge into surrounding eye anatomy in order retain the implant 105 in place and prevent the implant 105 from moving further into the suprachoroidal space SchS.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

The invention claimed is:

1. An eye treatment system, comprising:
   delivery system for delivering an ocular implant into an eye, the delivery system comprising:
   a) a proximal handle portion;
   b) a delivery portion coupled to the handle portion, the delivery portion configured to releasably couple to an ocular implant, the delivery portion including a retractable guidewire that fits through an inner lumen of the ocular implant such that only the guidewire is inserted through the inner lumen of the ocular implant when the ocular implant is attached to the guidewire;
   c) wherein the guidewire includes at least one non-spiraled curved section for providing an interference fit between the guidewire and an inner lumen of the ocular implant when the ocular implant is mounted on the guidewire to assist in retaining the implant on the guidewire during delivery into the eye, wherein the curved section of the guidewire is confined along a discrete section of the guidewire such that the discrete section of the guidewire forms a radius of curvature that is tighter than a radius of curvature of the entire guidewire and wherein the guidewire comprises at least two curved sections, the curved sections being spaced from one another a distance of about 0.0100 inch to 0.0200 inch along the length of the guidewire;
   d) an actuator that actuates to cause an ocular implant coupled to the delivery portion to release from the delivery portion upon actuation of the actuator; and
   the ocular implant.

2. The eye treatment system of claim 1, wherein the delivery portion further includes a sheath positioned axially over at least a portion of the guidewire.

3. The eye treatment system of claim 2, wherein the actuator includes a mechanism that includes a spring, the spring being coupled to the guidewire.

4. The eye treatment system of claim 3, wherein actuation of the actuator causes the spring to move the guidewire between a first position and a second position relative to the handle portion.

5. The eye treatment system of claim 4, wherein actuation of the actuator causes the spring to move the guidewire in a proximal direction relative to the handle portion.

6. The eye treatment system of claim 1, wherein the guidewire comprises an s-shape.

7. The eye treatment system of claim 1, wherein the guidewire comprises a sinusoidal curve shape.

8. The eye treatment system of claim 1, wherein, when the implant has been delivered into the eye, actuation of the actuator causes the guidewire to withdraw from the ocular implant in a proximal direction.

9. The eye treatment system of claim 1, wherein guidewire includes at least one inner lumen.

10. The eye treatment system of claim 9, wherein the delivery portion further includes a sheath positioned axially over at least a portion of the guidewire and wherein a distal end of the sheath abuts a proximal end of an ocular implant when the ocular implant is positioned on the guidewire, and wherein the distal end of the sheath prevents the ocular implant from moving toward the handle portion as the guidewire withdraws in a proximal direction.

11. The eye treatment system of claim 9, wherein the guidewire includes at least one opening that provides fluid communication between the inner lumen of the guidewire and an area surrounding the guidewire.

12. The eye treatment system of claim 11, wherein the area surrounding the guidewire comprises an inner lumen of an ocular implant.

13. The eye treatment system of claim 1, wherein the delivery system includes at least one fluid delivery feature which delivers fluid from a fluid source and into an inner lumen of the guidewire.

14. The eye treatment system of claim 13, wherein the fluid from the fluid source includes one or more of a viscoelastic, a drug and a stem cell.

15. The eye treatment system of claim 1, wherein the ocular implant is formed of a tubular structure having an internal lumen.

16. The eye treatment system of claim 1, wherein the ocular implant is configured to drain fluid from an anterior chamber of an eye to a supraciliary space of an eye.

17. The eye treatment system of claim 1, wherein a distal portion of the guidewire is configured to separate a ciliary body of the eye from a sclera of the eye.

18. The eye treatment system of claim 1, wherein the curved portion of the guidewire has a nominal longitudinal axis and one or more wire peaks separated from the nominal longitudinal axis, wherein each of the peaks contacts an inner surface of the ocular implant to assist in retaining the implant on the guidewire during delivery into the eye.

19. The eye treatment system of claim 1, further comprising a dampener coupled to the handle portion, the dampener adapted to dampen retraction of the guidewire upon actuation of the actuator.

* * * * *